US008703443B2

(12) United States Patent
Yamamoto et al.

(10) Patent No.: US 8,703,443 B2
(45) Date of Patent: Apr. 22, 2014

(54) γ-L-PGA PRODUCING MICROORGANISM, METHOD OF PRODUCING γ-L-PGA USING THE MICROORGANISM, CROSSLINKED SUBSTANCE PRODUCED USING THE MICROORGANISM, AND EXTERNAL DERMAL AGENT PRODUCED USING THE MICROORGANISM

(75) Inventors: Shuhei Yamamoto, Tsuruga (JP); Masaru Kitagawa, Tsuruga (JP); Michiko Suzuki, Otsu (JP); Atsushi Sogabe, Osaka (JP); Makoto Ashiuchi, Kochi (JP)

(73) Assignee: Toyo Boseki Kabushiki Kaisha, Osaka (JP)

(*) Notice: Subject to any disclaimer, the term of this patent is extended or adjusted under 35 U.S.C. 154(b) by 455 days.

(21) Appl. No.: 12/301,411

(22) PCT Filed: Mar. 12, 2007

(86) PCT No.: PCT/JP2007/054864
§ 371 (c)(1),
(2), (4) Date: Nov. 18, 2008

(87) PCT Pub. No.: WO2007/135801
PCT Pub. Date: Nov. 29, 2007

(65) Prior Publication Data
US 2009/0203790 A1 Aug. 13, 2009

(30) Foreign Application Priority Data

May 23, 2006 (JP) ................................ 2006-142685
Nov. 10, 2006 (JP) ................................ 2006-305894
Nov. 10, 2006 (JP) ................................ 2006-305897

(51) Int. Cl.
*C12P 21/06* (2006.01)

(52) U.S. Cl.
USPC ........................................ 435/69.1; 435/252.1

(58) Field of Classification Search
None
See application file for complete search history.

(56) References Cited

U.S. PATENT DOCUMENTS

2006/0105446 A1    5/2006    Sung et al.

FOREIGN PATENT DOCUMENTS

| CN | 1667019 A | 9/2005 | |
|---|---|---|---|
| EP | 1 557 152 A1 | 7/2005 | |
| EP | 2196534 A1 * | 6/2010 | ............... C12N 1/21 |
| JP | 07-135991 A | 5/1995 | |
| JP | 10-251402 A | 9/1998 | |
| JP | 2002-517204 A | 6/2002 | |
| JP | 2003-105081 A | 4/2003 | |
| JP | 2005-120032 A | 5/2005 | |
| JP | 2006-042617 A | 2/2006 | |
| WO | WO 2004/007593 A1 | 1/2004 | |

OTHER PUBLICATIONS

Hazayen et al., International Journal of Systematic and Evolutionary Microbiology, 2001, vol. 51, pp. 1133-1142.*

(Continued)

*Primary Examiner* — Alexander Kim
(74) *Attorney, Agent, or Firm* — Leydig, Voit & Mayer, Ltd.

(57) ABSTRACT

There are provided a microorganism characterized by producing poly-γ-L-glutamate with a molecular weight of 1,300,000 or greater and uniform optical purity under liquid culture conditions, a method of screening for the microorganism, a method of producing poly-γ-L-glutamate having large molecular weight by using the microorganism, and poly-γ-L-glutamate having an average molecular weight of 1,300,000 or greater. In addition, usages of these are provided.

9 Claims, 9 Drawing Sheets

(56) References Cited

OTHER PUBLICATIONS

Ashiuchi et al., Journal of Molecular Catalysis B: Enzymatic, 2003, vol. 23, pp. 249-255.*
Sung et al., Natural and Edible Biopolymer Poly-γ-glutamic Acid: synthesis, Production, and Applications, The Chemical Recored, 2005, vol. 5, pp. 352-366.*
Definition of strikethrough (last viewed on Mar. 28, 2013).*
Misono et al., Function and Biosynthetic Mechanism of Poly-.Gamma.-Glutamate, a Main Component of natto Mucilage., Vitamins (2005), vol. 79, pp. 71-78.*
Ashiuchi et al., Poly-ī³-glutamate depolymerase of *Bacillus subtilis*: production, simple purification and substrate selectivity., (2003) vol. 23, Issues 2-6, pp. 249-255.*
Ashiuchi et al., *Journal of Bioscience and Bioengineering*, 102(1): 60-65 (2006).
Ashiuchi et al., *Applied and Environmental Microbiology*, 70(7): 4249-4255 (Jul. 2004).
Park et al., *Journal of Molecular Catalysis B:Enzymatic*, 35: 128-133 (2005).
Suzuki et al., *Journal of Bacteriology*, 185(7): 2379-2382 (Apr. 2003).
Choi et al., *Radiat. Phys. Chem.*, 46(2): 175-179 (Aug. 1, 1995).
Kunioka et al., *Appl. Microbiol. Biotechnol.*, 47(5): 469-475 (1997).
Murakami et al., *Biomacromolecules*, 7(7): 2122-2127 (Jul. 2006).
Yang et al., *Journal of Biomedical Materials Research*, 62(1): 14-21 (2001).
"Enzyme Ultrastabilization of Archaebacteria-type Poly-γ-Glutamic Acid," Japan Society for Bioscience, Biotechnology, and Agrochemistry, Annual Meeting, Oral Presentation, Review (2006).
Hezayen et al., *Appl. Microbiol. Biotechnol.*, 54: 319-325 (2000).
Ashiuchi et al., *Japan Society for Bioscience, Biotechnology, and Agrochemistry, Annual Meeting 2006*, Oral Presentation, Review 292 (Mar. 5, 2006).
Yamamoto et al., *Japan Society for Bioscience, Biotechnology, and Agrochemistry, Annual Meeting 2002*, Oral Presentation, Review 297 (Mar. 5, 2002).
Aono et al., *Journal of Bacteriology*, 181(21): 6600-6606 (1999).
Ashiuchi et al., *Chemistry and Biology*, 40(4): 212-214 (2002).
Aschiuchi et al., *The Abstracts of the Society for Biotechnology, Japan, Annual Meeting*, p. 398 (2001).
Hezayen et al., *International Journal of Systematic and Evolutionary Microbiology*, 51: 1133-1142 (2001).
Imokawa, *Skin and Beauty*, 36(4): 210-228 (2004).
Makino et al., *Journal of Bacteriology*, 171(2): 722-730 (Feb. 1989).
Misono et al., *Vitamins*, 79(2): 71-78 (2005).
Weber, *The Journal of Biological Chemistry*, 265(17): 9664-9669 (1990).

* cited by examiner

F I G. 9
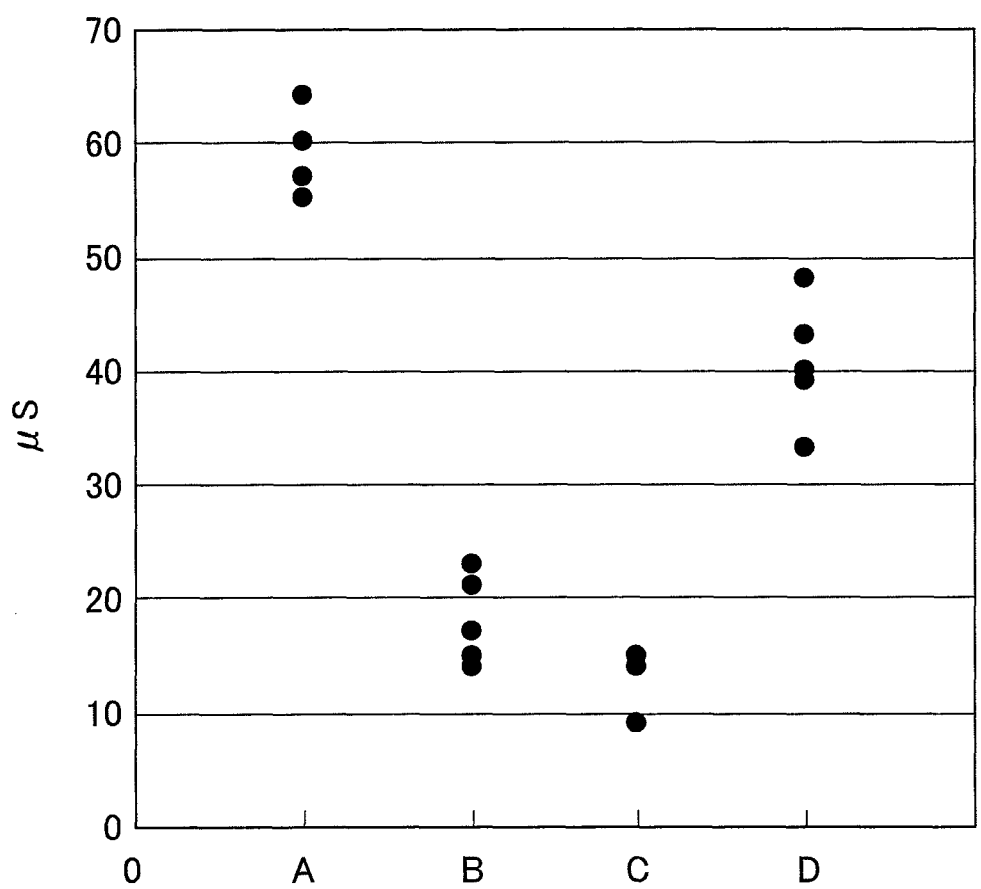

γ-L-PGA PRODUCING MICROORGANISM, METHOD OF PRODUCING γ-L-PGA USING THE MICROORGANISM, CROSSLINKED SUBSTANCE PRODUCED USING THE MICROORGANISM, AND EXTERNAL DERMAL AGENT PRODUCED USING THE MICROORGANISM

TECHNICAL FIELD

The present invention relates to microorganisms with high poly-γ-L-glutamate producing capability and their mutants, methods of producing poly-γ-L-glutamate using such a microorganism or mutant, and large-molecular-weight poly-γ-L-glutamate produced using such a microorganism or mutant.

The present invention relates also in general to crosslinked poly-γ-L-glutamate, methods of producing the acid, and hydrogels containing the acid, and in particular to crosslinked poly-γ-L-glutamate, with excellent water absorption and biodegradability, which is capable of being stably produced with desired quality, methods of producing the acid, and hydrogels containing the acid.

The present invention relates further in general to external dermal agents, and in particular to external dermal agents, containing at least either poly-γ-L-glutamate or crosslinked poly-γ-L-glutamate with high moisture retention, and suitable for use as moisture retention agents and cosmetics materials.

BACKGROUND ART

We are highly concerned in recent years about deteriorating global environment. Technological developments for recovery and protection of environment are urgently needed. There exists a consensus that environmental pollution is caused by progressively expanding human industrial activities, for example, waste water from factories. Meanwhile, we are now realizing that plastic products, so commonly found in our daily life that they have become indispensable in modern life, are no less impacting on environment. Many general-purpose plastics and synthetic polymers are produced chemically from petroleum. These chemical products are amazingly convenient due to their stability, light weight, strength, and low cost. Another fact about plastics is that they have been consumed and discarded without much thought for a long time. Today, many waste plastics are alleged to be threatening ecosystems because they do not decompose in natural environment. Depending how they are processed for disposal, they can be a source for dioxin and like environmental hormones (endocrine disrupting chemicals). We should not belittle the danger of plastics.

Growing awareness of environmental issues has brought biodegradability under a new spotlight, leading to the advent of a new concept "biodegradable plastics." A quick implementation of the concept is being awaited. A promising candidate for raw material for biodegradable plastics and hydrogels is biopolymer produced by microorganisms. Especially, the potential found in a class of biopolymer called polyamino acids which consist of a chain of amino acids with special forms of linkages is attracting a lot of interest. Three polyamino acids have been identified: poly-γ-glutamate ("PGA"), poly-ε-lysine, and cyanophycin.

Recent studies have revealed that the structural properties of polyamino acid (optical activity, type, molecular size, forms of linkages, etc. of constituent amino acid) strongly affect the functionality of the polyamino acid. PGA is a polyamino acid formed by amide bonding between α-amino groups and γ-carboxyl groups of glutamate. PGA is now well-known as the main substance of the sticky threads of Natto. The stickiness is largely due to the functionality in question. PGA is well-known for having both biodegradability and high water absorption. These functions are expected to find various applications in the food, cosmetics, medical products, and many other fields. A drawback of the currently commercialized PGA is that they are produced from *Bacillus subtilis* var. natto or their analogues. The result is chemically heteropolymers with both the optical isomers of the glutamate linked in a random manner. This fact presents a large obstacle in evaluating practical use of PGA as an alternative raw material to plastics.

There is a report about homopoly-γ-glutamate producing bacteria. For example, Non-patent Document 1 reports that *Bacillus anthracis* produces a poly-γ-D-glutamate consisting only of D-glutamate ("D-PGA"). However, the bacterium is highly pathogenic, hence unsuitable for use in PGA production on an industrial scale. Furthermore, the D-PGA produced has a low molecular weight. There is another report (Non-patent Document 2) that an alkalophilic bacterium, *Bacillus halodurans*, produces a poly-γ-L-glutamate ("L-PGA") consisting only of L-glutamate. However, the L-PGA produced by the bacterium also has a very low molecular weight.

A homopoly-γ-glutamate having relatively large molecular weight is reported to be produced by a halophilic archaebacterium, *Natrialba aegyptiaca*, which produces only poly-γ-L-glutamate having a molecular weight approximately from 100,000 to 1,000,000. This bacterium, however, has a molecular weight as low as about 100,000 in liquid culture. Also, the bacterium produces little poly-γ-L-glutamate and unsuited for industrial use. See Non-patent Document 3 and Patent Document 1.

Another poly-γ-L-glutamate producing organism is the hydra. The hydra however has the same, very low molecular weight problem. See Non-patent Document 4.

An application field for PGA is cosmetics. In applying PGA to cosmetics, PGA (water-soluble polymer compounds, in general) is required to have properties, such as uniform optical purity as well as high moisture retention and viscosity enhancement. To satisfy these two requirements at the same time, it is desirable that PGA should have uniform optical purity and large molecular weight.

Water absorbent resin is used in numerous fields: e.g., in disposable diaper and sanitary goods, for medical, construction, civil engineering, and architectural purposes, as texture enhancer, freshness-keeping agents for food, and important base materials for green engineering in the agricultural field such as gardening.

Among water absorbent resins, the acrylic ones are used in various fields owing to their excellent water absorption and low price. However, the acrylic water absorbent resins are hardly biodegradability. It is therefore difficult to process the acrylic water absorbent resins through decomposition by microorganisms. For example, they are not suitable for compost production or similar biological processing. When used in land filling, they remain there without decomposing.

Water absorbent resins addressing these problems are suggested. Patent Document 1, for example, discloses a biodegradable water absorbent resin composed of crosslinked poly-γ-glutamate. PGA is a polymer compound synthesized by various organisms and highly biodegradable. Patent Document 1 therefore evaluates the biodegradable water absorbent resin as being safely and easily disposable.

To summarize the discussion about conventional PGAs, most of them are formed from irregular linking of the two optical isomers, L-glutamate and D-glutamate, as is the case with the PGA in Patent Document 2. Some of the reported PGAs are formed from linking of only D-glutamate (Non-patent Document 1) and of only L-glutamate (Patent Document 1, Non-patent Documents 2 to 4).

In this specification, for convenience of description, PGA formed by the linking between D-glutamate and L-glutamate will be referred to as DL-PGA, PGA formed only from D-glutamate as D-PGA, and PGA formed only from L-glutamate as poly-γ-L-glutamate or L-PGA.

The biodegradable water absorbent resin of Patent Document 2 has a problem that the biodegradable water absorbent resin is difficult to stably produce with desired quality. It is also difficult in the first place to produce the crosslinked DL-PGA which constitutes the biodegradable water absorbent resin.

More specifically, the DL-PGA, or the starting material for the crosslinked DL-PGA disclosed in Patent Document 2, is synthesized by a Natto bacterium (e.g., *Bacillus subtilis*) or its analogue. In the DL-PGA obtained from a Natto bacterium or its analogue, however, D-glutamate and L-glutamate form irregular linkages; the content ratio and sequence of the D-glutamate and the L-glutamate change every time the PGA-producing bacterium is cultured. The crosslinked DL-PGA therefore has a different structure, hence different properties, from one molecule to the other. That will likely lead to quality difference depending on lots of the DL-PGA used in the production of the crosslinked substance, making it difficult to stably produce crosslinked PGA with desired quality.

Furthermore, it is generally believed that the starting material, DL-PGA, with inconsistent quality as in the case above makes it difficult to stably produce a crosslinked substance. The inventors of the present invention could not obtain crosslinked DL-PGA in research. This is presumably because DL-PGA, as mentioned earlier, has a different structure from one molecule to the other. In other words, the crosslinking efficiency in the production of crosslinked PGA depends on molecular structure. If individual molecules have an irregularly different structure, the crosslinking efficiency drops markedly. It is therefore difficult to crosslink DL-PGA in which each molecule has a different structure, and the yield of the crosslinked substance is very low.

Up until now, there are no reports at all that crosslinked L-PGA has been successfully obtained. This is presumably for the following reasons. No conventional liquid culture has successfully produced L-PGA with large average molecular weight. It is also a common technical knowledge that it is extremely difficult to obtain a crosslinked organic compound with a low molecular weight. These facts are so prohibitive that the person skilled in the art would not even conceive of obtaining low molecular weight crosslinked L-PGA. The result is a total lack of reports of attempts to obtain crosslinked L-PGA. Industrial purpose PGA is required to be producible by liquid culture because plate culture is hardly capable of producing large amounts of microorganisms, and collecting L-PGA from plate culture media is not efficient.

As an exemplary L-PGA synthesizing organism, Non-patent Document 1 discloses an alkalophilic bacterium, *Bacillus halodurans*, and Non-patent Document 2 discloses hydra. These organisms however can only synthesize L-PGA with very low molecular weights (no greater than 100,000).

Patent Document 2 and Non-patent Document 3 report that *Natrialba aegyptiaca*, a halophilic archaebacterium, produces L-PGA with molecular weights of about 100,000 to 1,000,000 if cultured on plate culture media. The L-PGA synthesized by *Natrialba aegyptiaca* in liquid culture, however, has a molecular weight of about 100,000, and its synthesis efficiency is very low.

Crosslinked D-PGA, even if ever obtained, is not suitable for industrial use.

A major reason is that the D-PGA synthesizing bacterium disclosed in Non-patent Document 4 is highly pathogenic *Bacillus anthracis*. The use of *Bacillus anthracis* in PGA producing for industrial purposes is utterly unsuitable.

There are two causes for rough skin. One is the peeling off of keratin cells. The other is deteriorating conditions of the skin in a dry atmosphere, which could lead to hardening of, hence damage to, epidermis. The rough skin due to desquamated keratin cells is caused, for example, by elution of intercorneocyte lipid, such as cholesterol, ceramide, and fatty acid; denaturation of keratin cells by ultraviolet rays and detergent; and hypoplasia of a keratin layer transmission barrier caused by interruption of balanced growth of epidermic cells and/or balanced keratinization.

Research activities have been underway about the synthesis of lipid components between keratin cells or similar intercorneocyte lipid and the delivery of the lipid components to the skin, for the purpose of prevention or treatment of rough skin. Lamella granules are biosynthesized by cells in a prickle layer and a granular layer and released between cells beneath a keratin layer, spreading to form a lamella structure. This substance present between cells is called intercorneocyte lipid.

Lamella granules contain, among other substances, glucosylceramide, cholesterol, ceramide, and phospholipid. Intercorneocyte lipid contains little glucosylceramide. In other words, the glucosylceramide in lamella granules is thought to be hydrolyzed by β-glucocerebrosidase and converted to ceramide. The ceramide then forms a lamella structure to facilitate the formation of keratin transmission barrier as an intercorneocyte lipid, acting as a barrier preventing rough skin. Especially, ceramide supplementation is reported in Non-patent Document 5 to be highly effective to rough skin caused by detergent and like material.

Meanwhile, to prevent rough skin due to hardened or damaged epidermis, external dermal agents with moisture retention effect, such as cosmetics, have been conventionally used. Use of an external dermal agent with moisture retention effect prevents evaporation of water via skin, allowing the epidermis and keratin layer to retain water. The function preserves the skin's homeostasis, hence moisture retention capability and softness, keeping the skin young and fresh.

Examples of conventionally reported lipophilic substances with skin moisture retention effect include vegetable oils, such as olive oil, and animal lipids, such as lanolin. Examples of hydrophilic substances with skin moisture retention effect include water-soluble polyhydric alcohols, such as glycerine, 1,3-butylene glycol, propylene glycol, and sorbitol; polysaccharides, such as hyaluronic acid and xanthan gum; water-soluble polymers, such as polyethylene glycol; salt of pyrrolidone carboxylic acid; natural moisture retention factors with low molecular weight (amino acid is a typical example); and vegetable extracts.

Like above examples, there are numerous kinds of substances with skin moisture retention effect. Those derived from animals and chemically synthesized are however avoided in recent years to follow the social trend for improved safety. For the same reason, substances derived from natural products and those obtained by fermentation by microorganisms are considered better. Furthermore, biodegradable materials, having much less negative impact not only on living things but also on environment, are regarded as being promising and receiving much attention.

Among biodegradable materials, the biopolymer produced by microorganisms is viewed as having good prospects. Especially, it has been discovered that a class of biopolymers called polyamino acid formed by condensation polymerization of amino acid have various functions and are receiving much attention for their potential capabilities. PGA, one of the polyamino acids, is of especially high interest.

PGA is a polyamino acid formed by amide bonding between α-amino groups and γ-carboxyl groups of glutamate, as mentioned earlier. PGA is a water absorbent polyamino acid known as the main substance of the sticky threads of Natto, a traditional Japanese favorite. The Japanese have a liking for Natto largely because of its attractive functionality. A known attractive function of PGA is a combination of biodegradability and high water absorption. Exploiting these functions, PGA is expected to find applications not only as cosmetics material as mentioned above, but also in the medical, food, and various other fields.

Nevertheless, some issues persist with the external dermal agents containing the conventional PGA. These agents are difficult to stably produce with desired quality and provide insufficient moisture retention.

The DL-PGA currently available as commercial products is chemically heteropolymers as mentioned earlier. Specifically, PGA is produced from a Natto bacterium or its analog. D-glutamate and L-glutamate form irregular linkages. The content ratio and sequence of the glutamates change every time the PGA-producing bacterium is cultured. Generally, the structural properties of polyamino acid (optical activity, type, molecular size, forms of linkages, etc. of constituent amino acid) strongly affect the functionality of the polyamino acid. The DL-PGA has a different structure, hence different properties, from one molecule to the other. That makes it difficult to stably produce DL-PGA with desired quality.

Furthermore, the DL-PGA, having insufficient moisture retention capability, poses large problems in developing commercial external dermal agents (e.g., cosmetics).

Up until now, there are no reports at all that an L-PGA-containing external dermal agent has been successfully produced. This is presumably for the following reasons.

Generally, when an external dermal agent is produced containing PGA, the PGA must have large molecular weight because the PGA is required to provide moisture retention capability. On the other hand, no conventional liquid culture has successfully produced L-PGA with large average molecular weight. This fact is so prohibitive that the person skilled in the art could not even conceive of producing an L-PGA-containing moisture retention agent.

In addition, as mentioned earlier, industrial purpose PGA is required to be producible by liquid culture. It is difficult to culture large amounts of microorganisms in a single process by plate culture, and collecting L-PGA from plate culture media is not efficient. In addition, D-PGA is not suitable for industrial use as mentioned earlier.

In Patent Document 2, crosslinked DL-PGA is used as a water absorbent resin. It is however difficult to use crosslinked DL-PGA as an external dermal agent.

The DL-PGA disclosed in Patent Document 2, the starting material for the crosslinked DL-PGA, is synthesized by a Natto bacterium (e.g., *Bacillus subtilis*) or its analogue. This method cannot be free from the inconsistent quality of the starting material (DL-PGA) and hardly produces a crosslinked substance in a stable manner. The inventors of the present invention could not obtain crosslinked DL-PGA in research. This is presumably because DL-PGA, as mentioned earlier, has a different structure from one molecule to the other. In other words, the crosslinking efficiency in the production of crosslinked PGA depends on molecular structure. If individual molecules have an irregularly different structure, the crosslinking efficiency drops markedly. It is therefore difficult to crosslink DL-PGA in which each molecule has a different structure, and the yield of the crosslinked substance is very low.

Thus, it is difficult to stably produce an external dermal agent with desired quality even by using crosslinked DL-PGA.

Meanwhile, up until now, there are no reports at all that crosslinked L-PGA has been successfully obtained.

This is because liquid culture has been never successful in producing L-PGA with large average molecular weight as mentioned earlier. It is a common technical knowledge that it is extremely difficult to obtain a crosslinked organic compound with a low molecular weight. These facts are so prohibitive that the person skilled in the art would not even conceive of obtaining low molecular weight crosslinked L-PGA. The result is a total lack of reports of attempts to obtain crosslinked L-PGA.

Crosslinked D-PGA, if ever obtained, is not suitable for industrial use because the only currently known D-PGA producing bacterium is *Bacillus anthracis* as mentioned earlier.

[Patent Document 1]
Published Japanese Translation of PCT Application No. 2002-517204 (Tokuhyo 2002-517204; published Jun. 18, 2002)

[Patent Document 2]
Japanese Unexamined Patent Publication No. 10-251402/1998 (Tokukaihei 10-251402; published Sep. 22, 1998)

[Non-Patent Document 1]
Makino, S., I. Uchida, N. Terakado, C. Sasakawa, and M. Yoshikawa, Molecular characterization and protein analysis of the cap region, which is essential for encapsulation in *Bacillus anthracis*, Journal of Bacteriology, 1989, 171, 722-730.

[Non-Patent Document 2]
Aono, R., M. Ito, and T. Machida, Contribution of the Cell Wall Component Teichuronopeptide to pH Homeostasis and Alkaliphily in the Alkaliphile *Bacillus lentus* C-125, Journal of Bacteriology, 1999, Vol. 181, 6600-6606.

[Non-Patent Document 3]
Hezayen, F. F., B. H. A. Rehm, B. J. Tindall and A. Steinbuchel, Transfer of *Natrialba asiatica* B1T to *Natrialba taiwanensis* sp. nov. and description of *Natrialba aegyptiaca* sp. nov., a novel extremely halophilic, aerobic, non-pigmented member of the Archaea from Egypt that produces extracellular poly(glutamic acid), International Journal of Systematic and Evolutionary Microbiology, 2001, 51, 1133-1142.

[Non-Patent Document 4]
Weber, J., Poly(gamma-glutamic acid)s are the major constituents of nematocysts in Hydra (Hydrozoa, Cnidaria), Journal of Biological Chemistry, 1990, Vol. 265, 9664-9669.

[Non-Patent Document 5]
Skin and Beauty, 36, 210 (2004)

DISCLOSURE OF INVENTION

The present invention, conceived in view of these background problems, has an objective of providing: a microorganism or its mutant, with uniform optical purity, which produces large amounts of poly-γ-L-glutamate; a method of producing poly-γ-L-glutamate having large molecular weight using the microorganism; and poly-γ-glutamate having large molecular weight and uniform optical purity.

The present invention has another objective of stably providing crosslinked L-PGA with desired quality.

The present invention has yet another objective of stably providing an external dermal agent with desired quality.

The inventors of the present invention have diligently worked and as a result found that the problems can be solved by the following means, which has led to the completion of the invention. The present invention has the following features.

1. A microorganism producing poly-γ-L-glutamate with a molecular weight of 1,300,000 or greater under liquid culture conditions.

2. The microorganism according to 1, wherein the poly-γ-L-glutamate has a molecular weight of 2,000,000 or greater.

3. The microorganism according to 1, wherein the poly-γ-L-glutamate has a molecular weight of 3,500,000 or greater.

4. The microorganism according to any one of 1 to 3, obtained by mutagenizing a microorganism having poly-γ-L-glutamate producing capability.

5. The microorganism according to 4, being mucoid under solid culture conditions with a NaCl concentration of 10% (w/v) or less.

6. The microorganism according to either one of 4 and 5, wherein the microorganism is a halophile.

7. The microorganism according to any one of 4 to 6, wherein the halophile is an extreme halophile.

8. The microorganism according to any one of 4 to 7, wherein the extreme halophile is archaebacterium.

9. The microorganism according to any one of 3 to 8, wherein the extremely halophilic archaebacterium is *Natrialba aegyptiaca*.

10. The microorganism according to any one of 1 to 9, wherein the microorganism is *Natrialba aegyptiaca*, strain 0830-82 (Accession No.: FERM BP-10747), *Natrialba aegyptiaca*, strain 0830-243 (Accession No.: FERM BP-10748), or *Natrialba aegyptiaca*, strain 0831-264 (Accession No.: FERM BP-10749).

11. A method of producing poly-γ-L-glutamate having large molecular weight, involving the steps of: culturing the microorganism according to any one of 1 to 10; and collecting poly-γ-L-glutamate having large molecular weight from a culture solution obtained by the culturing.

12. The method of producing poly-γ-L-glutamate having large molecular weight according to 11, wherein the culture solution contains 5 to 30 W/V % salt.

13. A poly-γ-L-glutamate having large molecular weight, obtained by the method of producing according to either one of 11 and 12.

14. A poly-γ-L-glutamate having an average molecular weight of 1,300,000 or greater.

15. A poly-γ-L-glutamate having an average molecular weight of 2,000,000 or greater.

16. A poly-γ-L-glutamate having an average molecular weight of 3,500,000 or greater.

17. *Natrialba aegyptiaca*, strain 0830-82 (Accession No.: FERM BP-10747), *Natrialba aegyptiaca*, strain 0830-243 (Accession No.: FERM BP-10748), or *Natrialba aegyptiaca*, strain 0831-264 (Accession No.: FERM BP-10749).

18. A method of screening for a poly-γ-L-glutamate producing mutant, involving at least the steps of: (a) mutagenizing a microorganism having poly-γ-L-glutamate producing capability; (b) culturing the mutagenized microorganism under solid culture conditions under which a parent strain forms no mucoid colonies so as to screen for a mucoid mutant; and (c) culturing the mutant obtained in (b) under liquid culture conditions so as to screen further for a mutant producing appreciably more poly-γ-L-glutamate than the parent strain.

19. A method of screening for a poly-γ-L-glutamate producing mutant, involving at least the steps of: (a) mutagenizing a microorganism having poly-γ-L-glutamate producing capability; (b) culturing the mutagenized microorganism under solid culture conditions with a NaCl concentration of 15% (w/v) or less so as to screen for a mucoid mutant; and (c) culturing the mutant obtained in (b) under liquid culture conditions so as to screen further for a mutant producing appreciably more poly-γ-L-glutamate than the parent strain.

20. A crosslinked poly-γ-L-glutamate, having a structure in which poly-γ-L-glutamate molecules are crosslinked.

21. The crosslinked poly-γ-L-glutamate according to 20, wherein the poly-γ-L-glutamate has an average molecular weight of 1,000,000 or greater.

22. The crosslinked poly-γ-L-glutamate according to 20, wherein the poly-γ-L-glutamate has an average molecular weight of 2,000,000 or greater.

23. The crosslinked poly-γ-L-glutamate according to 20, wherein the poly-γ-L-glutamate has an average molecular weight of 3,500,000 or greater.

24. The crosslinked poly-γ-L-glutamate according to any one of 20 to 23, having a water absorption ratio from 10 to 5,000, inclusive.

25. A hydrogel containing the crosslinked poly-γ-L-glutamate according to any one of 20 to 24.

26. A method of producing a crosslinked poly-γ-L-glutamate, involving the step of crosslinking molecules of a poly-γ-L-glutamate.

27. The method of producing a crosslinked poly-γ-L-glutamate according to 26, wherein the molecules of the poly-γ-L-glutamate are crosslinked in the step by irradiating the molecules with radiation.

28. The method of producing a crosslinked poly-γ-L-glutamate according to 27, wherein the radiation is gamma rays.

29. The method of producing a crosslinked poly-γ-L-glutamate according to 26, achieving a gelation ratio from 50% to 100%, inclusive, in the step.

30. The method of producing a crosslinked poly-γ-L-glutamate according to 26, further comprising the step of synthesizing the poly-γ-L-glutamate using *Natrialba aegyptiaca*.

31. The method of producing a crosslinked poly-γ-L-glutamate according to 30, wherein the *Natrialba aegyptiaca* is at least one bacterium strain selected from the group consisting of *Natrialba aegyptiaca*, strain 0830-82 (Accession No.: FERM BP-10747), *Natrialba aegyptiaca*, strain 0830-243 (Accession No.: FERM BP-10748), and *Natrialba aegyptiaca*, strain 0831-264 (Accession No.: FERM BP-10749).

32. An external dermal agent, containing at least either one of a poly-γ-L-glutamate and a crosslinked poly-γ-L-glutamate.

33. The external dermal agent according to 32, wherein the external dermal agent is a cosmetics material.

34. The external dermal agent according to 32, wherein the external dermal agent is a moisture retention agent.

Additional objectives, advantages and novel features of the invention will be set forth in part in the description which follows, and in part will become apparent to those skilled in the art upon examination of the following or may be learned by practice of the invention.

BRIEF DESCRIPTION OF DRAWINGS

[FIG. 9] A drawing showing results of a human skin roughness test in an example of the present invention.

BEST MODE FOR CARRYING OUT INVENTION

Figure 1:
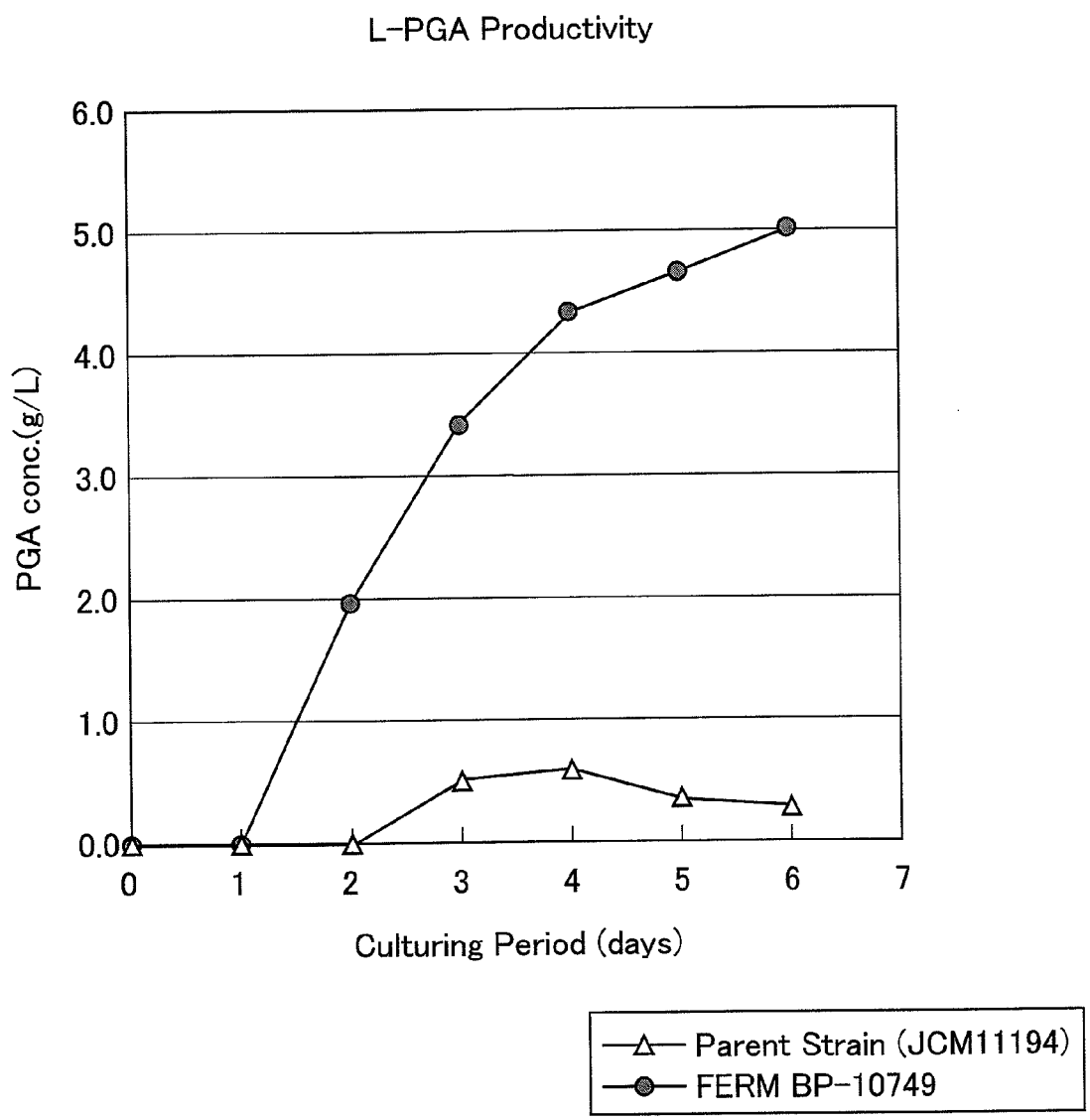
[FIG. 1] A drawing showing mutant poly-γ-L-glutamate productivity.

The following will describe an embodiment of the present invention. The description is by no means limiting the scope of the present invention. Variations are not to be regarded as a departure from the spirit and scope of the invention, and all modifications are intended to be included within the scope of the claims below.

<1. Microorganism with high poly-γ-L-glutamate Producing Capability or its Mutants, Method of Producing poly-γ-L-glutamate Using the Microorganism, and poly-γ-L-glutamate Having Large Molecular Weight>

Poly-γ-L-glutamate in the present invention is a homopolymer composed solely of L-glutamate. Its structure is shown represented by chemical formula (1), where n is the polymerization number of the poly-γ-L-glutamate.

[Chemical Formula 1]

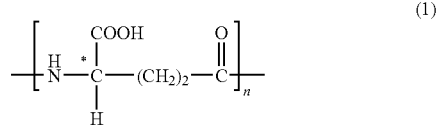

(1)

In the present invention, molecular weight is the number average molecular weight (Mn) calculated in terms of the molecular weight of an equivalent pullulan standard substance. The molecular weight is preferably 1,300,000 or greater, more preferably 2,000,000 or greater, and even more preferably 3,500,000 or greater.

The microorganism of the present invention can be any microorganism which produces poly-γ-L-glutamate having large molecular weight. Examples include wild microorganisms, their mutants, and those created by genetic engineering technology. Preferable examples are halophiles and strains created from them by mutagenization. The microorganism may be a thermophile, an extreme thermophile, a psychrophile, an acidophile, a barophile, or a cryophile, provided that it is sufficiently qualified as a halophile. The halophile of the present invention is a prokaryote which thrives at NaCl concentrations of 0.2 M or higher. The halophile may be either slight (which grows at 0.2-0.5 M NaCl concentrations), moderate (which grows at 0.5-2.5 M NaCl concentrations), or extreme (which grows at 2.5-5.2 M NaCl concentrations). The halophile is preferably an extreme halophile.

The halophile of the present invention may be an archaebacterium. Examples of archaebacteria include extremely halophilic archaebacteria (or "halophilic archaebacteria"), thermophilic archaebacteria, and methane bacteria (methanogenic archaebacteria). The halophile may be any archaebacterium provided that it can produce poly-γ-L-glutamate. Extremely halophilic archaebacteria are preferred. Most extreme halophiles are extremely halophilic archaebacteria. Some genera for extremely halophilic archaebacteria are *Halobacterium, Haloarcula, Haloferax, Halococcus, Halorubrum, Halobaculum, Natrialba, Natronomonas, Natronobacterium,* and *Natronococcus. Natrialba* is preferred, and *Natrialba aegyptiaca* is more preferred.

A colony is "mucoid" when it is viscous. The term refers to a polymer containing a polypeptide chain with principal posts covalently bonded to side chains of monosaccharide or polysaccharide. In this invention, "mucoid" refers to viscous colonies formed by poly-γ-L-glutamate bonded to polysaccharide.

One of the most important disclosures by the present invention is the method of obtaining a microorganism producing large amounts of poly-γ-L-glutamate. Another is a method of screening for the microorganism producing large amounts of poly-γ-L-glutamate. The microorganism may not be mutagenized, but is preferably subjected to such a process.

In the methods of obtaining and screening for the microorganism producing large amounts of poly-γ-L-glutamate of the present invention, an important disclose is to screen for a poly-γ-L-glutamate producing microorganism with increased salt sensitivity. The microorganism is screening for by culturing poly-γ-L-glutamate producing microorganisms under salt concentrations which normally do not facilitate production of poly-γ-L-glutamate and carry out selection focusing on mucoid colonies. Mutagenization may be done before or after the screening.

The salt sensitivity here refers to the sensitivity of a microorganism to concentration of salt at which the microorganism starts to produce poly-γ-L-glutamate. The microorganism or its mutant with increased salt sensitivity refers to a mutant producing poly-γ-L-glutamate, for example, even at 5% to 20% (W/V) NaCl concentrations and preferably to a mutant producing poly-γ-L-glutamate even at 7% to 15% (W/V) NaCl concentrations.

The salt is by no means limited in any manner and may be sodium, potassium, magnesium, manganese, calcium, zinc, iron, or any other general salt. Preferred among these examples is sodium.

The mutagenization may be done by any publicly known method: for example, by genetic engineering, having cells or spores come into contact with a mutagenic drug, or placing the microorganism under radiation (e.g. X-rays, γ-rays, or ultraviolet rays). Examples of the drug used in the "contact" method include alkylating agents, such as N-methyl-N'-nitro-N-nitrosoguanidine (NTG) and ethyl methanesulfonate (EMS). If any of these mutagenization methods are carried out, the survival rate of the microorganism for the mutagenization, although by no means limited in any particular manner, is preferably 1% or less.

The microorganism or its mutant obtained by the screening may be screened further for strains capable of producing poly-γ-L-glutamate in liquid culture.

He present invention has another benefit that the microorganism or its mutant capable of producing poly-γ-L-glutamate can now be readily obtained by liquid culture. It is not easy for a person skilled in the art to obtain, by liquid culture screening, not by the screening method above, a microorganism or its mutant capable of producing poly-γ-L-glutamate in liquid culture because in liquid culture screening, each colony obtained in solid culture needs to be liquid-cultured to check the amount of poly-γ-L-glutamate produced by the colony. This procedure must be repeated an astronomical number of times, which a person skilled in the art would readily appreciate is in practice impossible. The inventors of the present invention have diligently worked and have found the method of screening whereby a microorganism or its mutants capable of producing poly-γ-L-glutamate by liquid culture can be readily obtained. The present invention enables production of poly-γ-L-glutamate by liquid culture. That facilitates production of poly-γ-L-glutamate on an industrial scale, a great contribution to the development of industry.

Poly-γ-L-glutamate having large molecular weight can be produced on an industrial scale by liquid-culturing the microorganism or its mutants obtained by the present invention.

The liquid culture may be carried out by any method and conditions provided that the culturing allows the microorganism or its mutants obtained by the screening to grow and produce poly-γ-L-glutamate having large molecular weight. As an example, to culture the microorganism or its mutants obtained by screening, a culture medium is sterilized by an ordinary method, for example, at 110 to 140° C. for 8 to 20 minutes, before adding a mutant to the culture medium. In the case of extreme halophiles, the sterilization step may be omitted because they can grow in a NaCl-saturated environment where other microorganisms cannot grow.

If liquid culture is done, it may be done by shaking culture or ventilated stirring culture, to name a few examples. Proper culturing temperature in those cases are from 25 to 50° C., preferably from 30 to 45° C. The pH of the culture medium can be adjusted with sodium hydroxide, potassium hydroxide, ammonia, hydrochloric acid, sulfuric acid, or an aqueous solution of any of these substances. The pH may be of any value so long as it is adjustable. Desirable culturing pH is from 5.0 to 9.0, preferably from 6.0 to 8.5. The culturing period is generally from 2 to 4 days, but by no means limited so long as poly-γ-L-glutamate can be produced. In addition, salt may be added in culturing depending on the growth characteristics of the microorganism or mutants. The salt concentration in culturing is from 10 to 30%, preferably from 15 to 25%.

By the culturing under these conditions, poly-γ-L-glutamate accumulates primarily outside bacteria cells.

To separate poly-γ-L-glutamate from the culture, any of the following publicly known methods may be used: (1) Extraction from a solid culture using 20% or thinner saline solution (Japanese Unexamined Patent Publication No. 3-30648/1991 (Tokukaihei 3-30648)). (2) Precipitation with copper sulfate (Throne. B. C., C. C. Gomez, N. E. Noues and R. D. Housevright, J. Bacteriol., Vol. 68, page 307, 1954). (3) Alcohol precipitation (R. M. Vard, R. F. Anderson and F. K. Dean, Biotechnology and Bioengineering, Vol. 5, page 41, 1963). (4) Chromatography using a crosslinked chitosan mold as an adsorbent (Japanese Unexamined Patent Publication No. 3-244392/1991 (Tokukaihei 3-244392)). (5) Molecular ultrafiltration using a molecular ultrafiltration membrane. (6) Suitable combinations of (1) to (5). The substance obtained by the separation and collection steps can be regarded as a solution containing poly-γ-L-glutamate. The substance may, if necessary, be subjected to spray drying or freeze drying by a publicly known method to make it into powder form.

The following will describe in detail the microorganism, especially examples of *Natrialba aegyptiaca*, which by no means is limiting the present invention.

The following will describe a method of obtaining a microorganism or its mutants producing large amounts of poly-γ-L-glutamate having large molecular weight under liquid culture conditions by mutagenizing halophile, especially *Natrialba aegyptiaca*, a method of producing poly-γ-L-glutamate using the microorganism or its mutants, and also a method of obtaining poly-γ-L-glutamate having large molecular weight.

It is reported that *Natrialba aegyptiaca* produces only poly-γ-L-glutamate with molecular weights ranging approximately from 10 to 1,000,000 in solid culture. In contrast, under liquid culture conditions, *Natrialba aegyptiaca* reportedly produces only a small amount of poly-γ-L-glutamate, hence difficult to use for mass production, and produces poly-γ-L-glutamate with as low molecular weights as 100,000. Published Japanese Translation of PCT Application No. 2002-517204 (Tokuhyo 2002-517204) and F. F. Hezayen, B. H. A. Rehm, B. J. Tindall and A. Steinbuchel, Int. J. Syst. E., 51, 1133 (2001)

If a bacterium strain capable of producing poly-γ-L-glutamate under liquid culture conditions is to be screened for, since *Natrialba aegyptiaca* forms mucoid colonies on the surface of solid culture medium, single colonies tend to fuse and be difficult to separate. Even if the single colonies are successfully separated, every strain needs to be liquid-cultured separately from the others to check presence/absence of poly-γ-L-glutamate, which requires a huge amount of time and labor. The screening for such a bacterium strain is made possible for the first time by the advent of the present invention.

*Natrialba aegyptiaca* can grow in a culture medium containing 10% (w/v) or more salt. It is only when salt is added up to 20% (w/v) % or more that *Natrialba aegyptiaca* produces poly-γ-L-glutamate. In addition, *Natrialba aegyptiaca* is not mucoid under solid culture conditions with a NaCl concentration of 10% (w/v). Furthermore, the production of poly-γ-L-glutamate per bacteria cell is at least 10 times larger in solid culture than in liquid culture. These facts indicate that the present archaebacterium produces poly-γ-L-glutamate to tactfully protect itself from dehydration which could occur at high salt concentrations (Appl. Microbiol. Biotechnol., 54, 319 (2000)).

The inventors of the present invention have diligently worked and found that the *Natrialba aegyptiaca* modified in the present invention is mucoid under such conditions that the parent strain produces little poly-γ-L-glutamate, that is, solid culture conditions with a NaCl concentration of 10% (w/v), and produces appreciably more poly-γ-L-glutamate than the parent strain under liquid culture conditions.

The inventors have further found that the mutant produces poly-γ-L-glutamate having large molecular weight under liquid culture conditions.

The present invention is by no means limited to *Natrialba aegyptiaca*. In other words, the present invention discloses that the above method of screening, if applied to any poly-γ-L-glutamate producing halophile, provides a mutant producing appreciably more poly-γ-L-glutamate than the parent strain under liquid culture conditions. The present invention provides conventional unavailable mutants. In addition, halophiles can be cultured without sterilization because they can grow at high salt concentrations. With this particular feature which will lead to reductions in the cost of the culturing step, the halophiles provide promising substance producing systems. The present invention facilitates mass production of poly-γ-L-glutamate, a great contribution to the development of industry.

An ordinary mutagenization method is employed to obtain a microorganism with increased poly-γ-L-glutamate production capability from the above microorganisms as the parent strain. The mutagenization method can be any publicly known method, for example, by genetic engineering, having cells or spores come into contact with a mutagenic drug, or placing the parent strain under radiation (e.g., X-rays, γ-rays, or ultraviolet rays). Examples of the drug used in the "contact" method include alkylating agents, such as N-methyl-N'-nitro-N-nitrosoguanidine (NTG) and ethyl methanesulfonate (EMS). If any of these mutagenization methods are carried out, the survival rate of the microorganism for the mutagenization, although by no means limited in any particular manner, is preferably 1% or less.

For example, using an inoculation loop once, a sample is scraped off a single colony of N. aegyptiaca (JCM11194). The sample is inoculated on 3 mL of PGA-producing liquid culture medium 1 (22.5% NaCl, 2% $MgSO_4 \cdot 7H_2O$, 0.2% KCl, 3% trisodium citrate, 1% yeast extract, 0.75% casamino acid) in an 18-mL test tube and cultured at 37° C. and 300 rpm for 3 days. 0.5 mL of the obtained culture solution is inoculated on 50 mL of PGA-producing liquid culture medium 1 in a 500-mL Sakaguchi flask and cultured at 37° C. and 180 rpm for 5 days. The obtained culture solution is then centrifuged for 5 minutes at 3,000 rpm to collect bacteria cells to which a 100 mM buffer solution of citric acid (pH 6.0) is added. The mixture is resuspended. This procedure is repeated 3 times. 70%, 50%, 20%, and 10% NTG solutions, prepared by diluting an NTG-saturated solution (available from Tokyo Chemical Industry Co., Ltd.) with sterilized water, are added to aliquots of the suspended solution, up to ¹/₁₀th the quantity of the aliquots. The mixtures are then incubated at 42° C. and 150 rpm for 1 hour. Subsequent to the incubation, the mixtures are seeded on PGA-producing agar medium 1 (10% NaCl, 2% $MgSO_4 \cdot 7H_2O$, 0.2% KCl, 3% trisodium citrate, 1% yeast extract, 0.75% casamino acid, 2% agar) and cultured at 37° C. for 5 days. Desired single colonies of microorganisms are obtained under such conditions that the survival rate is less than or equal to 1%.

Strains capable of high poly-γ-L-glutamate yields are obtained, for example, by the following method. The colonies obtained by the mutagenization above is cultured for 2 to 4 days in an ordinary, publicly known nutrient medium (e.g., a culture medium containing broth, peptone, soy flour, yeast extract, casamino acid, amino acids, or their mixture) or an agar plate culture medium (e.g., an inorganic synthetic medium containing required nutrition), preferably in PGA-producing agar medium 1. Thereafter, each colony appearing on PGA-producing agar medium 1 are placed on both PGA producing agar plate culture medium 1 and PGA producing agar plate culture medium 2 (22.5% NaCl, 2% $MgSO_4 \cdot 7H_2O$, 0.2% KCl, 3% trisodium citrate, 1% yeast extract, 0.75% casamino acid, 2% agar) and static-cultured for 2 to 4 days.

Mutants forming mucoid colonies are selected also from PGA-producing agar medium 1, inoculated further on PGA-producing liquid culture medium 1 (22.5% NaCl, 2% $MgSO_4 \cdot 7H_2O$, 0.2% KCl, 3% trisodium citrate, 1% yeast extract, 0.75% casamino acid), and cultured at 37° C. and 1,180 rpm for 4 days. The poly-γ-L-glutamate contained in the culture medium is quantified. Mutants with high poly-γ-L-glutamate productivity when compared to wild strains are obtained in this manner.

The bacterium strains thus obtained have been deposited at the International Patent Organism Depository, National Institute of Advanced Industrial Science and Technology as Natrialba aegyptiaca, strain 0830-82 (Name of Depository: the International Patent Organism Depository, National Institute of Advanced Industrial Science and Technology, Date of Accession: Apr. 4, 2006, Accession Number: FERM BP-10747), Natrialba aegyptiaca, strain 0830-243 (Name of Depository: the International Patent Organism Depository, National Institute of Advanced Industrial Science and Technology, Date of Accession: Apr. 4, 2006, Accession Number: FERM BP-10748), and Natrialba aegyptiaca, strain 0831-264 (Name of Depository: the International Patent Organism Depository, National Institute of Advanced Industrial Science and Technology, Date of Accession: Apr. 4, 2006, Accession Number: FERM BP-10749).

To culture a mutant with increased poly-γ-L-glutamate productivity on the culture media, the mutant is added the culture media without the sterilization. If liquid culture is done, shaking culture or ventilated stirring culture are preferred, to name a few examples. Proper culturing temperature in those cases are from 30 to 50° C., preferably from 35 to 45° C. The pH of the culture medium can be adjusted with sodium hydroxide, potassium hydroxide, ammonia, hydrochloric acid, sulfuric acid, or an aqueous solution of any of these substances. The pH may be of any value so long as it is adjustable. Desirable culturing pH is from 5.0 to 9.0, preferably from 6.0 to 8.5. The culturing period is generally from 2 to 4 days. Desirable NaCl concentrations during the culturing are from 10 to 30%, preferably from 15 to 25%. Desirable yeast extract concentrations are 0.1 to 10%, preferably from 0.5 to 5.0%. For solid culturing, similarly to the liquid culturing above, the culturing temperature is from 30 to 50° C., preferably from 35 to 45° C.; the pH during culturing is from 5.0 to 9.0, preferably from 6.0 to 8.5; the NaCl concentration during culturing is from 10 to 30%, preferably from 15 to 25%; the yeast extract concentration is 0.1 to 10%, preferably from 0.5 to 5%. By the culturing under these conditions, poly-γ-L-glutamate accumulates primarily outside bacteria cells and contained in the culture.

Some methods of quantifying the poly-γ-L-glutamate in the culture solution are known: (1) The poly-γ-L-glutamate is precipitated with copper sulfate or ethanol from a sample containing poly-γ-L-glutamate. The precipitate is weighed, and the total nitrogen is measured by Kijerder method (M. Bovarnick, J. Biol. Chem., Vol. 145, page 415, 1942). (2) The quantity of glutamate after hydrochloric acid hydrolysis is measured (R. D. Housewrigt, C. B. Thorne, J. Bacteriol., Vol. 60, page 89, 1950). (3) A colorimetric method utilizing quantitative linking with a basic pigment (M. Bovarnick et al., J. Biol. Chem., Vol. 207, page 593, 1954). A preferred method is method (3).

Examples of the basic pigment include crystal violet, aniline blue, safranine-O, methylene blue, methyl violet, toluidine blue, congo red, azocarmine, thionine, and hematoxylin. Safranine-O is preferred.

A publicly known method may be used to separate and collect poly-γ-L-glutamate from the culture. For example, bacteria cells are removed by subjecting a culture solution to centrifugation. Subsequently, the obtained supernate fluid is diluted with 3 times the amount of water to adjust the pH to 3.0. After the pH adjustment, the diluted fluid is stirred at room temperature for 5 hours. Thereafter, ethanol is added to the fluid in a ratio of 3:1 to collect poly-γ-L-glutamate as a precipitate. The precipitate is dissolved in a 0.1-mM Tris-HCl buffer solution (pH 8.0) to remove low-molecular-weight substances by dialysis. After the dialysis, the obtained liquid is treated with DNase and RNase to remove nucleic acid and subsequently with proteinase to remove protein. After the proteinase treatment, low-molecular-weight substances are removed by dialysis. After the dialysis, dry poly-γ-L-glutamate is obtained by freeze drying. The glutamate may be purified using anion exchange resin where necessary. The glutamate can be however purified under general conditions.

Another one of the most important disclosures of the present invention is poly-γ-L-glutamate having large molecular weight and a method of obtaining that glutamate. Poly-γ-L-glutamate having large molecular weight can be obtained by using *Natrialba aegyptiaca* (*Natrialba aegyptiaca*), strain 0830-82 (Accession No.: FERM BP-10747), *Natrialba aegyptiaca* (*Natrialba aegyptiaca*), strain 0830-243 (Accession No.: FERM BP-10748), or *Natrialba aegyptiaca* (*Natrialba aegyptiaca*), strain 0831-264 (Accession No.: FERM BP-10749) of the present invention.

Large molecular-weight poly-γ-L-glutamate with a number average molecular weight of 1,300,000 or greater is obtained by culturing the three bacterium strains and purifying poly-γ-L-glutamate by the aforementioned method. The present invention has for the first time enabled the production of poly-γ-L-glutamate having such large molecular weight. Poly-γ-L-glutamate with molecular weight of 2,000,000 or greater, especially 3,500,000 or greater, can be also produced. Since the obtained poly-γ-L-glutamate has uniform optical purity and large molecular weight, it can be preferably used for cosmetics materials and like purposes.

<2. Crosslinked poly-γ-L-glutamate, Method of Producing it, and Acid-containing Hydrogel>

[Crosslinked L-PGA in Accordance with the Present Invention]

The crosslinked L-PGA in accordance with the present invention may be any L-PGA in which L-PGA molecules are crosslinked and is not limited in any particular manner in other specific structure.

L-PGA has uniform optical activity because it is composed solely of L-glutamate. For the same reason, each molecule show identical properties. Therefore, crosslinked L-PGA with desired quality can be stably obtained. The crosslinked L-PGA in accordance with the present invention is a homopolymer composed solely of L-glutamate and has a structure represented by formula (I).

In this specification, a "crosslinked structure" refers to a structure in which the molecules of a straight-chain polymer compound are linked either physically or chemically, a "crosslinked substance" refers, in this specification, to a polymer compound having physical or chemical properties changed by the possession of a crosslinked structure.

In the crosslinked L-PGA in accordance with the present invention, the L-PGA molecules are linked three-dimensionally by covalent bonds. Specifically, the L-PGA molecules are linked three-dimensionally by covalent bonds between non-hydrogen atoms in formula (I). In other words, the crosslinked L-PGA in accordance with the present invention is a polymer in which L-PGA molecules are three-dimensionally connected, that is, a network polymer constituted by L-PGA molecules. The bonding between the N of an L-PGA molecule and the rightmost C of an adjacent L-PGA molecule as in formula (I) is polymerization of the L-PGA molecules, not what is meant by the "crosslinked structure."

The average molecular weight of the L-PGA constituting the crosslinked L-PGA in accordance with the present invention is by no means limited so long as its molecules are crosslinked. The average molecular weight is however preferably 1,000,000 or greater, more preferably 2,000,000 or greater, even more preferably 3,500,000 or greater. With a molecular weight of 1,000,000 or greater, the L-PGA as a starting material produces a hydrogel with an improved gelation ratio, thereby improving hydrogel yield.

The greater the average molecular weight of the L-PGA, the more the water absorption ratio of the obtained crosslinked L-PGA is improved. Therefore, there is no particular upper limit for the average molecular weight of the L-PGA constituting the crosslinked L-PGA in accordance with the present invention. The method of producing L-PGA which will be detailed later can produce L-PGA with, for example, an average molecular weight of 6,000,000 and a maximum of 15,000,000.

The "average molecular weight" in this specification refers to the number average molecular weight (Mn) calculated in terms of the molecular weight of an equivalent pullulan standard substance.

The water absorption ratio of the crosslinked L-PGA in accordance with the present invention is not limited in any particular manner. The method of producing the crosslinked L-PGA in accordance with the present invention which will be detailed later can achieve, for example, from 10 to 5,000, inclusive, especially, from 1,900 to 4,400, inclusive. Especially, the PGA-based water absorbent resin that has a water absorption ratio in excess of 3,300 is a revolutionary PGA-based biodegradable water absorbent resin because such a resin was not obtainable with Patent Document 1 even when using DL-PGA.

In this specification, the "water absorption ratio" refers to a rate of increase in weight due to absorption by a substance of water and other hydrophilic liquids and its resultant swelling. The water absorption ratio of the crosslinked L-PGA in accordance with the present invention is calculated, for example, as follows. Crosslinked L-PGA powder is put into an enough amount of water for the crosslinked L-PGA to swell. After being left to sit in the water at 4° C. for 1 week for sufficient swelling, the mixture is placed on an 80-mesh gold net to remove water. From the wet weight of the resultant L-PGA, the dry weight of the crosslinked L-PGA powder is subtracted. The obtained value is then divided by the dry weight of the crosslinked L-PGA powder to calculate the water absorption ratio.

The crosslinked L-PGA in accordance with the present invention is preferably composed solely of L-PGA, but may contain DL-PGA molecules and D-PGA molecules. To produce crosslinked L-PGA with invariable quality, however, the DL-PGA and D-PGA molecules preferably account for from 0 wt % to 20 wt %, inclusive.

[Method of Producing Crosslinked L-PGA in Accordance with the Present Invention]

The method of producing the crosslinked L-PGA in accordance with the present invention only needs to include a crosslinking step of crosslinking L-PGA molecules. By crosslinking the L-PGA, composed solely of L-glutamate, which has uniform optical activity as a starting material, each molecule of the crosslinked L-PGA come to have the same properties. Hence, crosslinked L-PGA with desired quality is stably produced.

The L-PGA is dissolved in a solvent to obtain an L-PGA solution which is subsequently subjected to a crosslinking reaction. The solvent dissolving the L-PGA is by no means limited so long as it can dissolve the L-PGA. Examples include water, alcohol, acetone, methyl acetate, and ethyl acetate. Among them, water, methyl alcohol, and ethyl alcohol are preferred. Water is the most preferred among the examples. The concentration of the L-PGA when the L-PGA is dissolved in one of these solvents is not limited in any particular manner. The concentration is preferably from 1 wt % to 10 wt %, inclusive, more preferably from 2 wt % to 8 wt %, inclusive, and even more preferably from 2 wt % to 7 wt %, inclusive. The pH of the L-PGA solution is not limited in any particular manner. The pH is preferably from 5.0 to 9.0, inclusive, and more preferably from 6.0 to 8.0, inclusive.

As the L-PGA solution goes through a crosslinking reaction, crosslinked L-PGA forms in the solution, and the crosslinked L-PGA swells by absorbing the solvent. A hydrogel is thus obtained. This is one of embodiments of the hydrogel in accordance with the present invention which will be detailed later. Furthermore, by freeze drying the hydrogel, the solvent is removed, leaving the crosslinked L-PGA containing no solvent. The hydrogel in accordance with the present invention will be detailed later.

The method of producing the crosslinked L-PGA in accordance with the present invention produces L-PGA with a gelation ratio, for example, from 50% to 100%, inclusive, and especially from 70% to 100%, inclusive, in the aforementioned crosslinking reaction.

The "gelation ratio" in this specification refers to the weight percentage of the crosslinked L-PGA produced in the crosslinking reaction to the L-PGA as the starting material. In other words, the "gelation ratio" is the yield of the obtained crosslinked L-PGA or eventually hydrogel to the L-PGA as a starting material. Specifically, the ratio is calculated by diving the dry weight of the hydrogel obtained by the crosslinking reaction by the dry weight of the L-PGA subjected to the crosslinking reaction and multiplying the result by 100.

The method of conducting the L-PGA crosslinking reaction is by no means limited so long as L-PGA molecules are crosslinked. Any conventional, publicly known method may be used. For example, a crosslinking agent may be used. Radiation may be used. Of these, use of radiation is preferred. Use of radiation does not require removal a crosslinking agent after crosslinking reaction and enables production of high purity crosslinked L-PGA.

The radiation that may be used in the method of producing the crosslinked L-PGA in accordance with the present invention is not limited in any particular manner. Alpha rays, beta rays, gamma rays, electron rays, neutron radiation, and X-rays may be used. Of these, gamma rays are preferred. Gamma rays may be generated by conventional, publicly known method or equipment. for example, by using an irradiator containing cobalt 60 as the radiation source.

The exposure radiation dose for the L-PGA is preferably from 0.5 kGy to 20 kGy, inclusive, more preferably from 2 kGy to 10 kGy, inclusive, and even more preferably from 3 kGy to 7 kGy, inclusive. The dose is set to a suitable value according to the usage of the produced crosslinked L-PGA and other factors. Generally, a high radiation dose produces a hard hydrogel, and a low radiation dose produces a soft hydrogel. For example, if the radiation dose is 1 kGy or 3 kGy, the resultant hydrogel exhibits such high fluidity that the hydrogel spreads horizontally under no external force when placed on a flat plate. if the radiation dose is 5 kGy or 7 kGy, the resultant hydrogel exhibits such low fluidity that the hydrogel stays still without spreading horizontally when placed on a flat plate.

If the L-PGA is irradiated for crosslinking, the L-PGA solution may be placed in a container that is transparent to the radiation. Such containers are not limited in any particular manner, and examples include vials and other glass containers.

After placing the L-PGA solution in a container transparent to radiation, the solution may be immediately irradiated. Preferably, however, the solution is bubbled with nitrogen before irradiation. Removing oxygen from the solution prevents disruption of crosslinking reaction.

If a crosslinking agent is used to crosslink the L-PGA, the agent may be an epoxy compound, a polysaccharide containing a carboxylic acid group and/or carboxylate group, an amino acid, or another conventional, publicly known crosslinking agent. The agent is not limited in any particular manner. For example, The epoxy compound is, for example, glycerine triglycidyl ether, di-glycerine polyglycidyl ether, poly-glycerine polyglycidyl ether, or polyoxyethylene sorbitol polyglycidyl ether. The polysaccharide is, for example, a mixture of glucose, fructose, galactose, and glucuronic acid, a mixture of rhamnose, glucose, galactose, and glucuronic acid, or a polycarboxylic acid primarily composed of hyaluronic acid. The amino acid is, for example, polyasparaginic acid, polylysine, asparaginic acid, lysine, arginine, or a mixture of them. These substances may be used singly or if necessary in a proper combination of two or more.

The L-PGA used in the method of producing the crosslinked L-PGA in accordance with the present invention is by no means limited so long as the molecules of the L-PGA can be crosslinked. As mentioned earlier, however, the L-PGA preferably has a large average molecular weight.

Furthermore, the L-PGA used in the method of producing the crosslinked L-PGA in accordance with the present invention may be given in salt form, for example, sodium salt, potassium salt, magnesium salt, or calcium salt. Among them, sodium salt is preferred.

The L-PGA used in the method of producing the crosslinked L-PGA in accordance with the present invention may be prepared by any conventional, publicly known method. For example, the L-PGA may be prepared using an L-PGA producing microorganism.

The L-PGA producing microorganism is by no means limited so long as the microorganism synthesizes L-PGA. The microorganism may be, for example, a wild type of the L-PGA producing microorganism, a mutant of it, or a microorganism with L-PGA producing capability given or enhanced by genetic engineering technology. Among these microorganisms, halophile with L-PGA producing capability is a preferred example halophilic archaebacterium with L-PGA producing capability is a more preferred example, and extremely halophilic archaebacterium with L-PGA producing capability is an even more preferred example.

Examples of the extremely halophilic archaebacterium include *Halobacterium, Haloarcula, Haloferax, Halococcus, Halorubrum, Halobaculum, Natrialba, Natronomonas, Natronobacterium*, and *Natronococcus*. A preferred example is *Natrialba*. A more preferred example is *Natrialba aegyptiaca*. An even more preferred example is at least one bacterium strain selected from the group consisting of *Natrialba aegyptiaca*, strain 0830-82 (Accession No.: FERM BP-10747), *Natrialba aegyptiaca*, strain 0830-243 (Accession No.: FERM BP-10748), and *Natrialba aegyptiaca*, strain 0831-264 (Accession No.: FERM BP-10749). Using *N. aegyptiaca*, one can obtain L-PGA with relatively large molecular weight. Especially, any of the bacterium strains, *N. aegyptiaca* FERM BP-10747, *N. aegyptiaca* FERM BP-10748, and *N. aegyptiaca* FERM BP-10749, is capable of synthesizing L-PGA with an average molecular weight 1,000,000 or greater under liquid culture conditions. These strains therefore have a high yield for crosslinked L-PGA and high producing efficiency for L-PGA.

*N. aegyptiaca* FERM BP-10747, *N. aegyptiaca* FERM BP-10748, and *N. aegyptiaca* FERM BP-10749 are mutants of *N. aegyptiaca* found independently by the inventors of the present invention using the screening and mutagenization methods described later in example 2. Like these examples, a strain of *N. aegyptiaca* which produces L-PGA with large average molecular weight may be screened for by the screening and/or mutagenization method for use in the method of producing the crosslinked L-PGA in accordance with the present invention. In this specification, the simply expression, "*N. aegyptiaca*," encompasses mutants of the *N. aegyptiaca*.

The following will describe an embodiment of the method of producing L-PGA using *N. aegyptiaca*. The method is however by no means limited to this embodiment.

The culture medium in which to culture *N. aegyptiaca* is not limited in any particular manner so long as the *N. aegyptiaca* can growth and synthesize L-PGA. Preferably, the culture medium is a liquid culture medium. Use of a liquid culture medium enables culturing of a large amount of *N. aegyptiaca* in a single process, which extremely improves L-PGA producing efficiency.

The composition of the culture medium used for the *N. aegyptiaca* culturing is by no means limited so long as the medium contains carbon source and inorganic salts that can be ingested by *N. aegyptiaca*. The medium may also contain, if necessary, yeast extract and other nutrients. As an example, the inventors of the present invention use a culture medium containing 22.5% NaCl, 2% $MgSO_4.7H_2O$, 0.2% KCl, 3% Trisodium Citrate, 1% yeast extract, 0.75% casamino acid to culture *N. aegyptiaca* FERM BP-10749 in the examples which will be detailed later. Yeast extract, if added to the culture medium, preferably has a concentration of from 0.1 wt % to 10 wt %, inclusive, more preferably from 0.5 wt % to 5.0 wt %, inclusive.

Since *N. aegyptiaca* is an extreme halophile, salt may be added to the culture medium according to the growth characteristics of *N. aegyptiaca* used for L-PGA production. During culturing, the salt concentration is from 10 wt % to 30 wt %, inclusive, and preferably from 15 wt % to 25 wt %, inclusive.

The pH of the culture medium used in the *N. aegyptiaca* culturing is not limited in any particular manner. The pH is however preferably from 5.0 to 10, inclusive, and more preferably from 6.0 to 8.5, inclusive. The pH may be adjusted with sodium hydroxide, potassium hydroxide, ammonia, hydrochloric acid, sulfuric acid, or an aqueous solution of any of these substances. The pH may be of any value so long as it is adjustable.

After preparing the culture medium, it is sterilized by an ordinary method, and *N. aegyptiaca* used for the L-PGA production is added for culturing. The culture medium may be sterilized by a conventional, publicly known method. For example, the culture medium is sterilized at 110 to 140° C. for 8 to 20 minutes. The sterilization step may be omitted by raising the NaCl concentration in the culture medium to saturation. *N. aegyptiaca*, being an extreme halophile as mentioned earlier, can grow in a culture medium saturated with NaCl, whereas other microorganisms cannot.

If *N. aegyptiaca* is liquid-cultured, shaking culture or ventilated stirring culture, as examples, are preferred. Culturing temperature, although not limited in any particular manner, is preferably from 25° C. to 50° C., inclusive, and more preferably from 30° C. to 45° C., inclusive.

The culturing period for *N. aegyptiaca* is not limited in any particular manner and may be set to a suitable value depending on other culturing conditions and a target amount of L-PGA produced. The period is, for example, about 2 to 4 days.

Culturing *N. aegyptiaca* under these culturing conditions, L-PGA accumulates primarily outside bacteria cells.

The method of separating and collecting L-PGA from the culture medium after culturing *N. aegyptiaca* is not limited in any particular manner. The method may be a conventional, publicly known method. Specifically, methods (1) to (6) described under the heading, <1>, may be used.

The following is a description of a method, as an example, of separating and collecting the L-PGA from the culture medium after culturing *N. aegyptiaca*. The method is however by no means limited to the example.

First, after culturing *N. aegyptiaca*, bacteria cells are removed from the culture solution by, for example, centrifugation. L-PGA is then precipitated in the obtained supernatant by adding ethanol or a like lower alcohol. The precipitate is preferably dissolved in a suitable buffer solution to remove impurities by, for example, dialysis. The inventors of the present invention, will be described later in examples, collected L-PGA by diluting the supernatant from which bacteria cells have been collected with 3 times the amount of water, adjusting the pH to 3.0, stirring at room temperature for 5 hours, and adding 3 times the amount of ethanol to cause precipitation. The inventors dissolved the precipitate in a 0.1-mM Tris-HCl buffer solution (pH 8.0) and dialyzed the solution to remove impurities.

The dialysis may not completely remove nucleic acid and protein. Therefore, the solution is preferably further treated with DNase, RNase, and proteinase. Subsequent to the treatment, the solution may be dialyzed or subjected to another purification process to obtain high purity L-PGA.

By this process, a solution containing L-PGA can be obtained. Furthermore, crosslinked L-PGA in powder form can be obtained by freeze drying the obtained solution. The solution may be purified if necessary. The purification may be done by a conventional, publicly known method, for example, by dialysis or using an anion exchange resin.

To produce crosslinked L-PGA containing DL-PGA molecules and D-PGA molecules, DL-PGA molecules and/or D-PGA molecules are mixed with the L-PGA solution and subjected the crosslinking reaction detailed above.

[Hydrogel in Accordance with the Present Invention]

The hydrogel in accordance with the present invention contains the crosslinked L-PGA in accordance with the present invention. Since the hydrogel in accordance with the present invention contains the crosslinked L-PGA, the hydrogel is colorless, transparent, and biodegradable.

The "hydrogel" in this specification refers to a gel formed by a polymer which has swollen by absorbing water or another solvent. In other words, it is a polymer swollen with solvent, constituted primarily by a polymer and a solvent or like water content. Hydrogel contains large amounts of water, is in an intermediate state between liquid and solid, and differs from liquid in that it has zero fluidity. When squeezed or otherwise pressurized, the solvent in the hydrogel does not seep out.

Hence, the hydrogel in accordance with the present invention is an entity swollen with a solvent, constituted primarily by a crosslinked L-PGA and a solvent.

The hydrogel in accordance with the present invention, as described in relation to the method of producing the crosslinked L-PGA in accordance with the present invention, can be obtained by carrying out crosslinking reaction on a solution prepared by dissolving L-PGA in water or another solvent.

The hydrogel in accordance with the present invention can be obtained by adding water or another solvent to the crosslinked L-PGA in powder form. If the hydrogel is prepared with a small amount of the solvent, the obtained hydrogel can absorb more water and other solvents, exhibiting excellent water absorption. Furthermore, the solvent absorbed by the crosslinked L-PGA constituting the hydrogel in accordance with the present invention does not seep out of the hydrogel. Therefore, the hydrogel in accordance with the present invention has excellent moisture retention capability.

The hydrogel in accordance with the present invention may be granulated into a predetermined uniform shape. Alternatively, the hydrogel may be, for example, irregularly pulverized or spherical. Application fields for the hydrogel are not limited to health care, but also include many other fields: e.g. as moisture retention agents and other cosmetics, disposable diapers and other toiletries, body fluid absorbents and other medical products and soil modifiers.

Examples of moisture retention agents (cosmetics) include face care products, hand care products, body care products, foot care products, head care products, and hair care products, nail care products, and mouth care products.

Embodiments of the present invention will be described in more detail by way of example below. Needless to say, the present invention is by no means limited to the examples. Details could vary. Furthermore, the present invention is not limited to the description of the embodiments above, and may be altered by a skilled person within the scope of the claims. An embodiment based on a proper combination of technical means disclosed in different embodiments is encompassed in the technical scope of the present invention.

<3. External Dermal Agent>

[External Dermal Agent in Accordance with the Present Invention]

The external dermal agent in accordance with the present invention contains at least either L-PGA or crosslinked L-PGA. Otherwise, the arrangement is not limited in any particular manner.

L-PGA, made up of linked L-glutamate, has uniform optical activity, and its molecules have uniform properties. The crosslinked L-PGA obtained from L-PGA can be stably produced with desired quality. Therefore, an external dermal agent with desired quality can be stably provided by using at least either L-PGA or crosslinked L-PGA.

Furthermore, the L-PGA and crosslinked L-PGA have excellent moisture retention capability. The external dermal agent in accordance with the present invention can be used preferably as moisture retention agents and/or cosmetics materials.

If the external dermal agent in accordance with the present invention is used as a moisture retention agent, specific, preferred application examples include face care products, hand care products, body care products, foot care products, head care products, hair care products, nail care products, and mouth care products.

If the external dermal agent in accordance with the present invention is used as a cosmetics material, specific, preferred application examples include face care products, such as milky lotion, essence, facial cream and lotion, facial wash, and makeup remover, hand care products, body care products, foot care products, head care products, hair care products, nail care products, and mouth care products.

In this specification, "skin" or "dermal" refers to the skin of the face, neck, breast, back, arms, legs, hands, feet, and head. The "external dermal agent" in this specification refers to a chemical used to improve dry skin, rough skin, and other skin conditions or preventing such skin conditions from becoming worse.

(L-PGA)

The L-PGA contained in the external dermal agent in accordance with the present invention is a homopolymer composed of linked L-glutamate. The L-PGA has a structure of formula (1).

A suitable average molecular weight is selected for the L-PGA contained in the external dermal agent in accordance with the present invention, depending on the usage of the external dermal agent and other conditions. The average molecular weight is preferably 1,300,000 or greater, more preferably 2,000,000 or greater, and even more preferably 3,500,000 or greater.

The greater the average molecular weight of the L-PGA, the further improved the moisture retention capability of the external dermal agent containing the L-PGA. Therefore, there is no particular upper limit for the average molecular weight of the L-PGA. The method of producing L-PGA which will be detailed later can produce L-PGA with, for example, an average molecular weight of 6,000,000 and a maximum of 15,000,000.

The "average molecular weight" is defined as under the heading, <1>.

The L-PGA contained in the external dermal agent in accordance with the present invention may be obtained by any one of various conventional, publicly known methods. For example, the L-PGA is obtained using a microorganism which produces L-PGA-("L-PGA producing microorganism").

(L-PGA Producing Microorganism)

The L-PGA producing microorganism is by no means limited so long as the microorganism synthesizes L-PGA. The microorganism may be, for example, a wild type of the L-PGA producing microorganism, a mutant of it, or a microorganism with L-PGA producing capability given or enhance by genetic engineering technology. Specifically, those microorganisms described under the headings, <1> and <2>, are preferred.

Conventionally, it has been difficult to screen for PGA producing microorganisms under liquid culture conditions for the following reasons. For example, if *N. aegyptiaca* forms mucoid colonies on the surface of solid culture medium, single colonies tend to fuse and be difficult to separate. Even if the single colonies are successfully separated, every strain needs to be liquid-cultured separately from the others to check production of L-PGA, which requires a huge amount of time and labor. The external dermal agent in accordance with the present invention is a completely novel external dermal agent and made possible for the first time by the use of the bacterium which is obtained by the method of screening found independently by the inventors of the present invention and which produces L-PGA with large molecular weight, (Method of Producing L-PGA)

The method of producing L-PGA described under the headings, <1> and <2>, is preferably used here. No further description is given.

A solution containing L-PGA is obtained by the process described above. If the obtained solution is freeze-dried, crosslinked L-PGA powder is obtained. In addition, the solution may be purified if necessary. The purification may be done by a conventional, publicly known method, for example, by dialysis or using an anion exchange resin, as mentioned earlier.

(Crosslinked L-PGA)

The crosslinked L-PGA contained in the external dermal agent in accordance with the present invention only needs to have the L-PGA molecules being crosslinked. Otherwise, the arrangement is not limited in any particular manner.

The "crosslink and "crosslinked L-PGA" are defined the same way as under the heading, <2>, The average molecular weight of the L-PGA constituting the crosslinked L-PGA contained in the external dermal agent in accordance with the present invention is by no means limited so long as its molecules are crosslinked. The average molecular weight is preferably 1,000,000 or greater, more preferably 2,000,000 or greater, and even more preferably 3,500,000 or greater. With a molecular weight of 1,000,000 or greater, the L-PGA as a starting material produces a hydrogel with an improved gelation ratio, thereby improving hydrogel yield.

The greater the average molecular weight of the L-PGA, the more the water absorption ratio of the obtained crosslinked L-PGA is improved. Therefore, there is no particular upper limit for the average molecular weight of the L-PGA constituting the crosslinked L-PGA in accordance with the present invention.

The water absorption ratio of the crosslinked L-PGA contained in the external dermal agent in accordance with the present invention is not limited in any particular manner. The method of producing the crosslinked L-PGA in accordance with the present invention which will be detailed later can achieve, for example, from 10 to 5,000, inclusive, especially, from 1,900 to 4,400, inclusive. Especially, the PGA-based water absorbent resin that has a water absorption ratio in excess of 3,300 is a revolutionary PGA-based biodegradable water absorbent resin because such a resin was not obtainable with Patent Document 2 even when using DL-PGA.

The "water absorption ratio" is defined the same way as under the heading, <2>.

The crosslinked L-PGA contained in the external dermal agent in accordance with the present invention is preferably composed solely of L-PGA, but may also contain DL-PGA molecules and D-PGA molecules. To produce crosslinked L-PGA with invariable quality, however, the DL-PGA and D-PGA molecules preferably account for from 0 wt % to 20 wt %, inclusive.

(Method of Producing Crosslinked L-PGA)

The method of producing the crosslinked L-PGA contained in the external dermal agent in accordance with the present invention only needs to include a crosslinking step of crosslinking L-PGA molecules. Specifically, the method is the same as the one described under the heading, <2>.

The L-PGA used to produce the crosslinked L-PGA contained in the external dermal agent in accordance with the present invention only needs to be obtained by one of various conventional, publicly known methods. Examples of such L-PGA were given above.

When a crosslinked L-PGA is produced containing DL-PGA and D-PGA molecules, the DL-PGA and/or D-PGA molecules are mixed with the aforementioned L-PGA solution, and the resultant solution is subjected to the aforementioned crosslinking reaction.

The crosslinked L-PGA contained in the external dermal agent in accordance with the present invention may be a hydrogel containing the crosslinked L-PGA. Specific examples were given under the heading, <2>.

(Composition of External Dermal Agent)

The concentration of at least one of the L-PGA and the crosslinked L-PGA in the external dermal agent in accordance with the present invention is not limited in any particular manner. If only the L-PGA is contained, the concentration is preferably from 0.00001 to 30 wt %, and more preferably from 0.0001 to 20 wt %. If only the crosslinked L-PGA is contained, the concentration is preferably from 0.00001 to 30 wt %, and more preferably from 0.0001 to 20 wt %. If both the L-PGA and the crosslinked L-PGA are contained, the total amount is preferably from 0.00001 to 30 wt %, more preferably from 0.0001 to 20 wt %. Within these ranges, the resultant agent has little odor, good colors, and high moisture retention capability. The external dermal agent is very useful for applications in moisture retention agents and/or cosmetics materials.

The external dermal agent in accordance with the present invention only needs to produced by dissolving at least one of the L-PGA and the crosslinked L-PGA in a conventional, publicly known solvent. The solvent used in the production of the external dermal agent in accordance with the present invention is not limited in any particular manner. A preferred example is water.

The external dermal agent in accordance with the present invention may include suitable additives according to the usage and other conditions provided that the additives do not interfere with the effects of the present invention. Typical examples of the additives include additives commonly used in cosmetics materials, quasi-drugs, and pharmaceuticals that are applied externally to skin: for example, hydrocarbons, oils and like oil components, waxes, silicones, alcohols, fatty acids, oxidation inhibitors, antibacterial agents, ultraviolet absorbing agents, drugs, purified water or other water content, vegetable extracts, neutralizing agents, moisture retention agents other than the L-PGA and crosslinked L-PGA, thickening agents, antiseptics, surfactants, fragrant materials, coloring agents, and various skin nutrients.

The following will name concrete examples of the additives, but examples are by no means limited to those included here. These substances may be used singly or if necessary in a proper combination of two or more.

Examples of the hydrocarbons include liquid paraffin, squalane, micro crystalline wax, ceresin wax, paraffin wax, and petrolatum.

Examples of the oils include avocado oil, camellia oil, macadamia nuts oil, olive oil, lanolin, castor oil, olive oil, grape seed oil, cacao seed oil, coconut oil, vegetable waxes, jojoba oil, and like vegetable oils.

Examples of the waxes include jojoba oil, carnauba wax, candelilla wax, bee wax, and whale wax.

Examples of the silicones include dimethyl polysiloxane and methylphenyl siloxane.

Examples of the alcohols include higher alcohols, such as caprylic alcohol, lauryl alcohol, myristyl alcohol, cetyl alcohol, cholesterol, phytosterol, cetanol, stearyl alcohol, hexyldecanol, and octyldodecanol; and lower alcohols, such as ethanol.

Examples of the fatty acids include higher fatty acids, such as capric acid, myristic acid, palmitic acid, stearic acid, behenic acid, lanolin fatty acid, linoleic acid, linolenic acid, lauric acid, oleic acid, and isostearic acid.

Examples of the oxidation inhibitors include butylhydroxytoluene, tocopherol, and phytin.

Examples of the antibacterial agents include benzoic acid, salicylic acid, sorbic acid, p-hydroxybenzoate alkylester, and hexachlorophen.

Examples of the ultraviolet absorbing agents include p-aminobenzoic acid-based ultraviolet absorbing agents, anthranilic acid-based ultraviolet absorbing agents, salicylic acid-based ultraviolet absorbing agents, cinnamic acid-based ultraviolet absorbing agents, benzophenone-based ultraviolet absorbing agents, sugar-based ultraviolet absorbing agents, 3-(4'-methylbenzylidene)-d-camphor, 3-benzylidene-d, 1-camphor, urocanic acid, urocanic acid ethyl ester, 2-phenyl-5-methylbenzoxazole, 2,2'-hydroxy-5-methylphenyl benzotriazole, 2-(2'-hydroxy-5'-t-octylphenyl)benzotriazole, 2-(2'-hydroxy-5'-methylphenyl benzotriazole, dibenzaladine, dianisoyl methane, and 4-methoxy-4'-t-butyl dibenzoyl methane, 5-(3,3-dimethyl-2-norbornylidene)-3-pentan-2-one.

Examples of the drugs include amino acids, such as glycine, alanine, valine, leucine, threonine, phenylalanine, tyrosine, asparaginic acid, asparagine, glutamine, taurine, arginine, and histidine, and alkali metal salts and hydrochlorides of these amino acids; organic acids, such as acyl sarcosinate (e.g., sodium lauroyl sarcosinate), glutathione, citric acid, malic acid, tartaric acid, and lactic acid; nicotinamide, benzyl nicotinate, γ-oryzanol, allantoin, glycyrrhizinate, glycyrrhetic acid and its derivative, hinokitiol, bisabolol, eucalyptone, thymol, inositol, saponins, such as psychosaponin, carrot saponin, gourd saponin, and soapberry saponin, pantothenyl ethyl ether, ethinyl estradiol, tranexamic acid, arbutin, cepharanthin, and placenta extracts.

Examples of the various skin nutrients include vitamin A and its derivatives, vitamin B2, pantothenic acid and its derivatives, niacin, biotin, and mixtures of these substances.

The neutralizing agents are not limited in any particular manner. Examples include potassium hydroxide, sodium hydroxide, sodium carbonate, sodium hydrogen carbonate, disodium hydrogen phosphate, sodium acetate, 2-amino-2-methyl-1-propanol, 2-amino-2-methyl-1,3-propanediol, and triethanol amine.

Examples of the surfactants include non-ion surfactants, such as polyoxyethylene lauryl ether, polyoxyethylene sorbintan fatty acid ester, polyoxyethylene cetyl ether, polyoxyethylene stearyl ether, polyoxyethylene oleyl ether, polyoxyethylene higher alcohol ether, polyoxyalkyl allyl ether, polyoxyethylene distyrenated phenyl ether, polyoxyethylene derivatives, sorbitan monolaurate, sorbitan monooleate, sorbintan sesquioleate, sorbintan monolaurate, polyoxyethylene monolaurate, polyoxyethylene sorbitan laurate, polyoxyethylene sorbitan monostearate, polyoxyethylene sorbitan monooleate, 1-polyoxyethylene sorbitan monolaurate, polyoxyethylene sorbitan monooleate, polyoxyethylene sorbitan tetraoleate, polyethylene glycol monolaurate, polyethylene glycol monooleate, polyoxyethylenated hard castor oil, polyoxyethylenated castor oil, and polyoxyethylene lanolin; and glycine-based, imidazoline-based, L-arginine-based, and L-lysine-based amphoteric surfactants, alkylamine betaine, and like amphoteric surfactants.

Examples of the moisture retention agents other than the L-PGA and crosslinked L-PGA include polyhydric alcohols, such as glycerine, propylene glycol, 1,3-butylene glycol, and polyethylene glycol; sugars, such as glucose, sorbitol, dextrin, trehalose, and lactose, and their derivatives; amino acids and their derivatives, such as sodium glutamate, keratin derivatives, collagen derivatives, and trimethyl glycine; water-soluble polymers, such as carboxy vinyl polymers, sodium chondroitin sulfate, sodium hyaluronate, sodium pyrrolidone carboxylate, and sodium lactate; various moisture-retaining vegetable extracts, such as seaweed extracts and yeast extracts, and mixtures of these substances; esters, such as isopropyl palmitate, isopropyl myristate, octyldodecyl myristate, octyldodecyl oleate, and cholesteryl oleate; and sodium polyacrylate; crystalline cellulose; various essential oils; and mixtures of these substances. The aforementioned vegetable oils, waxes, fatty acids, and higher alcohols may also be used as the moisture retention agents.

Examples of the thickening agents include water-soluble polysaccharides, such as xanthan gum; water-soluble celluloses, such as hydroxymethylcellulose sodium, methylcellulose, and hydroxyethylcellulose; and water-soluble polymers, such as pullulan and sodium polyacrylate.

Examples of the antiseptics include parabens, salicylic acids, benzoate, phenoxyethanol, and chlorhexidine gluconate.

Examples of the fragrant materials include vanillin, orange flavor, lemon flavor, milk flavor geraniol, and linalool.

Examples of the coloring materials include natural pigments, such as water-soluble tar-based pigments, water-insoluble tar-based pigments, gardenia-based pigments, safflower-based pigments, turmeric-based pigments, paprika pigments, annatto pigments, and cochineal pigments; and acid and basic pigments.

Other vegetable extracts may also added. Examples include sorrel, sophorae radix, spatterdock, orange, sage, yarrow, mallow, sialid, thyme, angelicae radix, spruce, birch, equisetum, gourd, marronnier, meadow saxifrage, arnica, lily, tansy, peony, aloe, gardenia, sawara cypress, and white lily.

The following will describe the embodiments of the present invention in more detail by way of examples. Needless to say, the present invention is by no means limited to the examples. Details could vary. Furthermore, the present invention is not limited to the aforementioned embodiments above, and may be altered within the scope of the claims. An embodiment based on a proper combination of technical means disclosed in different embodiments is encompassed in the technical scope of the present invention.

The entire contents of academic papers and patent documents cited in this specification are incorporated herein by reference. Throughout the examples below, all incidents of "%" should be read as "wt %."

EXAMPLES

The following will describe the present invention in concrete terms by means of examples. The present invention is by no means limited to the examples.

Example 1

NTG Mutagenization Method

Using an inoculation loop once, a sample was scraped off a single colony of N. aegyptiaca (JCM11194; purchased from the Riken Institute of Physical and Chemical Research). The sample was inoculated on 3 mL of PGA-producing liquid culture medium 1 (22.5% NaCl, 2% $MgSO_4.7H_2O$, 0.2% KCl, 3% trisodium citrate, 1% yeast extract, 0.75% casamino acid, pH 7.2) in an 18-mL test tube and cultured at 37° C. and 300 rpm for 3 days. 0.5 mL of the obtained culture solution was inoculated on 50 mL of PGA-producing liquid culture medium 1 in a 500-mL Sakaguchi flask and cultured at 37° C. and 180 rpm for 5 days. The obtained culture solution was then centrifuged for 5 minutes at 3,000 rpm to collect bacteria cells to which a 100 mM buffer solution of citric acid (pH 6.0) was added. The mixture was resuspended. This procedure was repeated 3 times. 70%, 50%, 20%, and 10% NTG solutions, prepared by diluting an NTG-saturated solution (available from Tokyo Chemical Industry Co., Ltd.) with sterilized water, were added to aliquots of the suspended solution, up to 1/10th the quantity of the aliquots. The mixtures were then incubated at 42° C. and 150 rpm for 1 hour. Subsequent to the incubation, the mixtures were seeded on PGA-producing agar medium 1 (10% NaCl, 2% $MgSO_4.7H_2O$, 0.2% KCl, 3% trisodium citrate, 1% yeast extract, 0.75% casamino acid, 2% agar) and cultured at 37° C. for 5 days.

Conditions (70% NTG-saturated solution) were set up under which the survival rate was less than or equal to 1%.

Example 2

Screening for Bacterium Producing Large Amounts of poly-γ-L-glutamate

A colony obtained under the conditions under which the survival rate is less than or equal to 1% was seeded on PGA-producing agar medium 1 (10% NaCl, 2% $MgSO_4.7H_2O$, 0.2% KCl, 3% trisodium citrate, 1% yeast extract, 0.75% casamino acid, 2% agar) and PGA-producing agar medium 2 (22.5% NaCl, 2% $MgSO_4.7H_2O$, 0.2% KCl, 3% Trisodium Citrate, 1% yeast extract, 0.75% casamino acid, 2% agar) and cultured at 37° C. for 6 days. After the culturing, a mutant was selected which produced poly-γ-L-glutamate under the culturing conditions in PGA-producing liquid culture medium 1. The obtained mutant was again seeded in PGA-producing agar medium 1 to confirm reproducibility. Using an inoculation loop once, a sample was scraped off a single colony of the mutant of which the reproducibility was confirmed. The sample was inoculated on 3 mL of PGA-producing liquid culture medium 1 in an 18-mL test tube and cultured at 37° C. and 300 rpm for 3 days. 0.5 mL of the obtained culture solution was inoculated on 50 mL of PGA-producing liquid culture medium 1 in a 500-mL Sakaguchi flask and cultured at 37° C. and 180 rpm for 3 days. The culture medium was diluted 5 fold, and the poly-γ-L-glutamate in the culture medium was measured by a safranine method. Mutants were screened for which had increased poly-γ-L-glutamate productivity over the parent strain. 30,000 strains were screened by the aforementioned method. As a result, 3 strains of mutants which produced large amounts of poly-γ-L-glutamate were obtained.

The bacterium strains thus obtained were deposited with the International Patent Organism Depositary, National Institute of Advanced Industrial Science and Technology, as *Natrialba aegyptiaca*, strain 0830-82 (Accession No.: FERM BP-10747), *Natrialba aegyptiaca*, strain 0830-243 (Accession No.: FERM BP-10748), and *Natrialba aegyptiaca*, strain 0831-264 (Accession No.: FERM BP-10749).

Example 3

Comparison of poly-γ-L-glutamate Productivity of Mutants

Strain 0831-264 (Accession No.: FERM BP-10749), obtained in example 2, and the parent strain (JCM11194) were cultured under the same culturing conditions as in example 2. As illustrated in FIG. 1, FERM BP-10749 exhibited a poly-γ-L-glutamate productivity of 4.99 g/L in the culture solution, whereas the parent strain exhibited a productivity of 0.61 g/L.

Example 4

Purifying of poly-γ-L-glutamate

Using an inoculation loop once, a sample was scraped off a single colony of a strain, Accession Number FERM BP-10749, obtained in the example above. The sample was inoculated on 3 mL of PGA-producing liquid culture medium 1 (22.5% NaCl, 2% $MgSO_4.7H_2O$, 0.2% KCl, 3% trisodium citrate, 1% yeast extract, 0.75% casamino acid) in five 18-mL test tubes and cultured at 37° C. and 300 rpm for 3 days. 0.5 mL of the obtained culture solutions were inoculated on 50 mL PGA-producing liquid culture medium 1 in ten 500-mL Sakaguchi flasks and cultured at 37° C. for 5 days. The obtained culture solutions were then centrifuged to remove bacteria cells. Subsequently, the obtained supernate fluid was diluted with 3 times the amount of water to adjust the pH to 3.0. After the pH adjustment, the diluted fluid was stirred at room temperature for 5 hours. Thereafter, ethanol was added to the fluid in a ratio of 3:1. The mixture was subjected to centrifugation to collect poly-γ-L-glutamate as a precipitate. The precipitate was dissolved in a 0.1-mM Tris-HCl buffer solution (pH 8.0) to remove low-molecular-weight substances by dialysis. After the dialysis, $MgCl_2$ and, DNaseI (available from TAKARA Co.), and RNaseI (available from NIPPON GENE Co. Ltd.) were added to the obtained liquid up to 1 mM, 10 U/mL, and 20 μg/mL to remove nucleic acid, and the mixture was incubated at 37° C. for 2 hours. Next, proteinase K (available from TAKARA Co.) was added up to 3 U/mL to remove protein, and the mixture was incubated at 37° C. for 5 hours. After the treatment with proteinase K, the mixture was dialyzed with Milli Q water to remove low-molecular-weight substances. After the dialysis, poly-γ-L-glutamate was adsorbed by an anion exchange resin, Q sepharose Fast Flow (available from Amersham Biosciences). After the resin was washed, the glutamate was eluted with 1-M NaCl. The obtained solution was dialyzed with Milli Q water. The solution obtained in the dialysis was freeze dried to obtain a Na salt of poly-γ-L-glutamate.

Example 5

GPC Analysis of Na Salt of poly-γ-L-glutamate

The average molecular weight of the obtained a Na salt of poly-γ-L-glutamate was measured by GPC analysis. IR analysis was also conducted.

Figure 2:
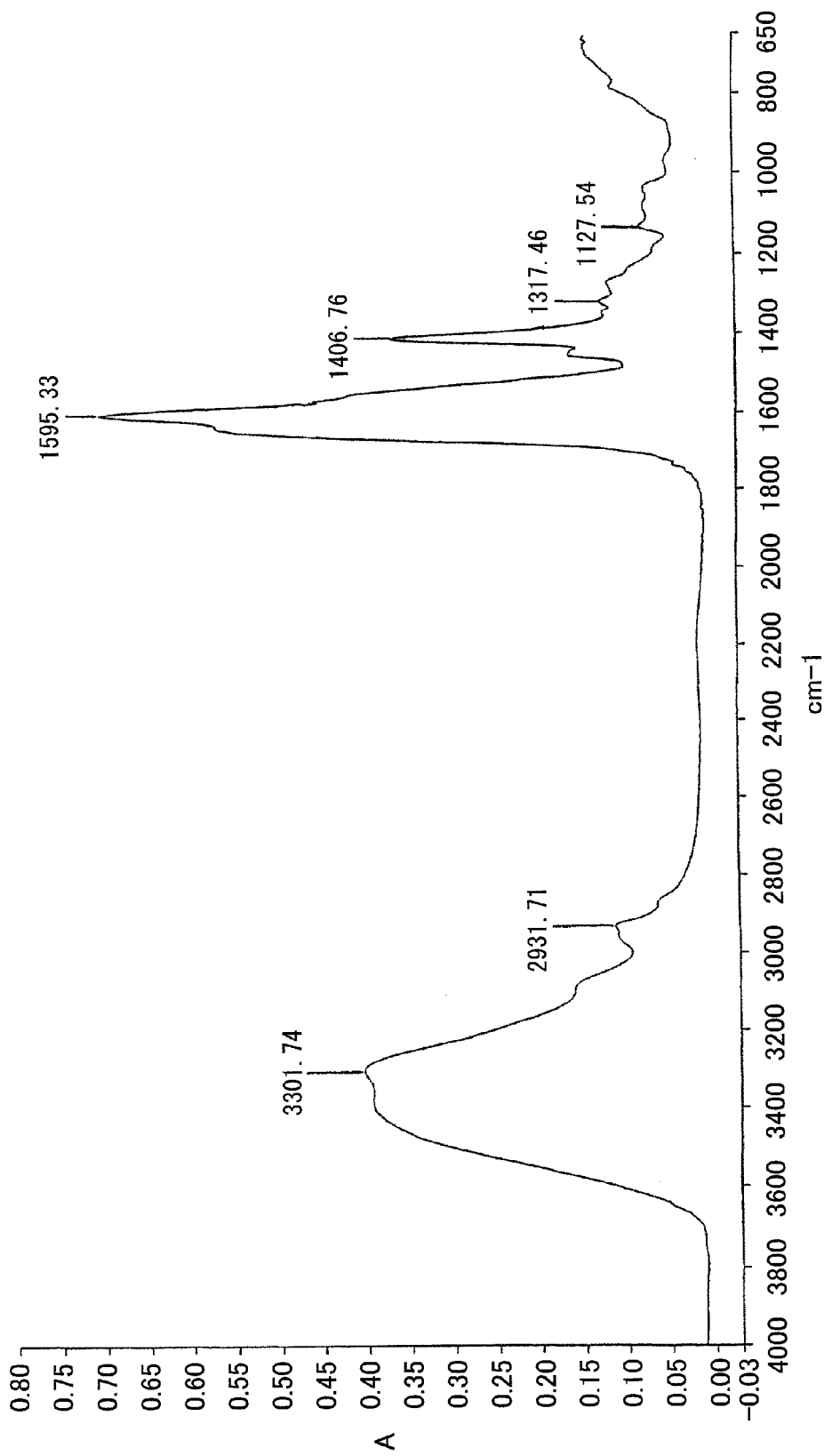
[FIG. 2] A drawing showing results of IR the analysis of poly-γ-L-glutamate .Na salt.

The GPC analysis revealed that Mw was 7,522,000, Mn was 3,704,000, and Mw/Mn was 2.031 (in terms of equivalent pullulan). The conditions for the GPC analysis are listed below:

Device: HLC-8220 GPC (available from Tosoh Corporation)
Column: TSKgel α-M (available from Tosoh Corporation)
Flow rate: 0.6 mL/min
Eluent: 0.15-M aqueous solution of NaCl
Column temperature: 40° C.
Amount supplied: 10 μL
Detector: Differential thermal analyzer The IR analysis confirmed that the substance was a Na salt (see FIG. 2).

Example 6

GPC Analysis and IR Analysis of Free poly-γ-L-glutamate

In the purification step for poly-γ-L-glutamate in example 4, poly-γ-L-glutamate was adsorbed by an anion exchange resin, Q sepharose Fast Flow (available from Amersham Biosciences). After the resin was washed, the glutamate was eluted with 1-M NaCl. Subsequently, the pH of the solution containing poly-γ-L-glutamate was adjusted to pH 2.0 using 1-N HCl. Thereafter, the solution was dialyzed with Milli Q water and then freeze dried to obtain free poly-γ-L-glutamate. The average molecular weight of the obtained free poly-γ-L-glutamate was measured by GPC analysis. IR analysis was also conducted.

Figure 3:
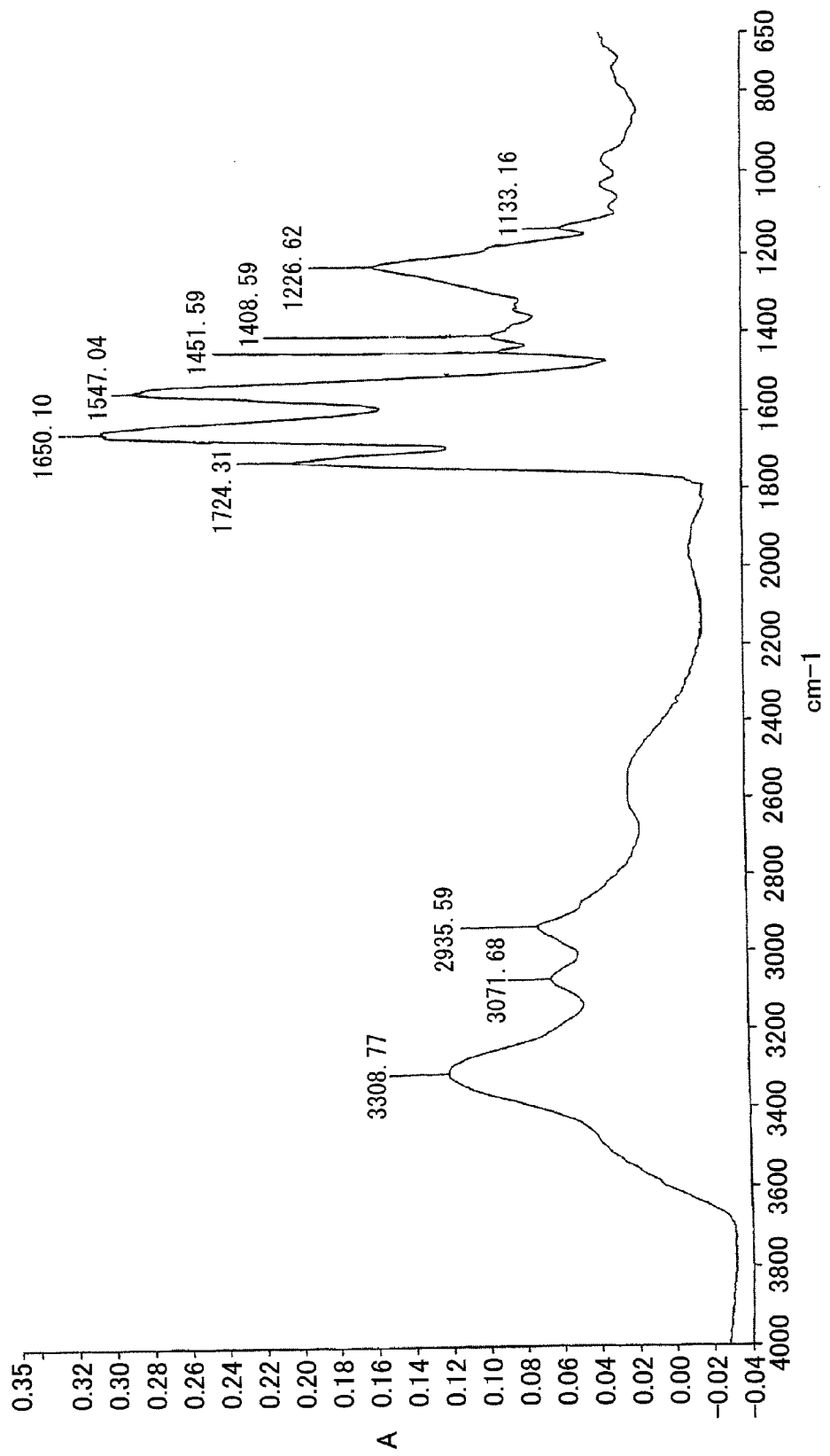
[FIG. 3] A drawing showing results of IR the analysis of free poly-γ-L-glutamate.

The GPC analysis revealed that Mw was 2,888,000, Mn was 1,327,000, and Mw/Mn was 2.176 (in terms of equivalent pullulan). The conditions for the GPC analysis are the same as in example 5. The IR analysis confirmed that the substance was free poly-γ-L-glutamate (see FIG. 3).

Example 7

Verification of poly-γ-L-glutamate Structure

Figure 4:
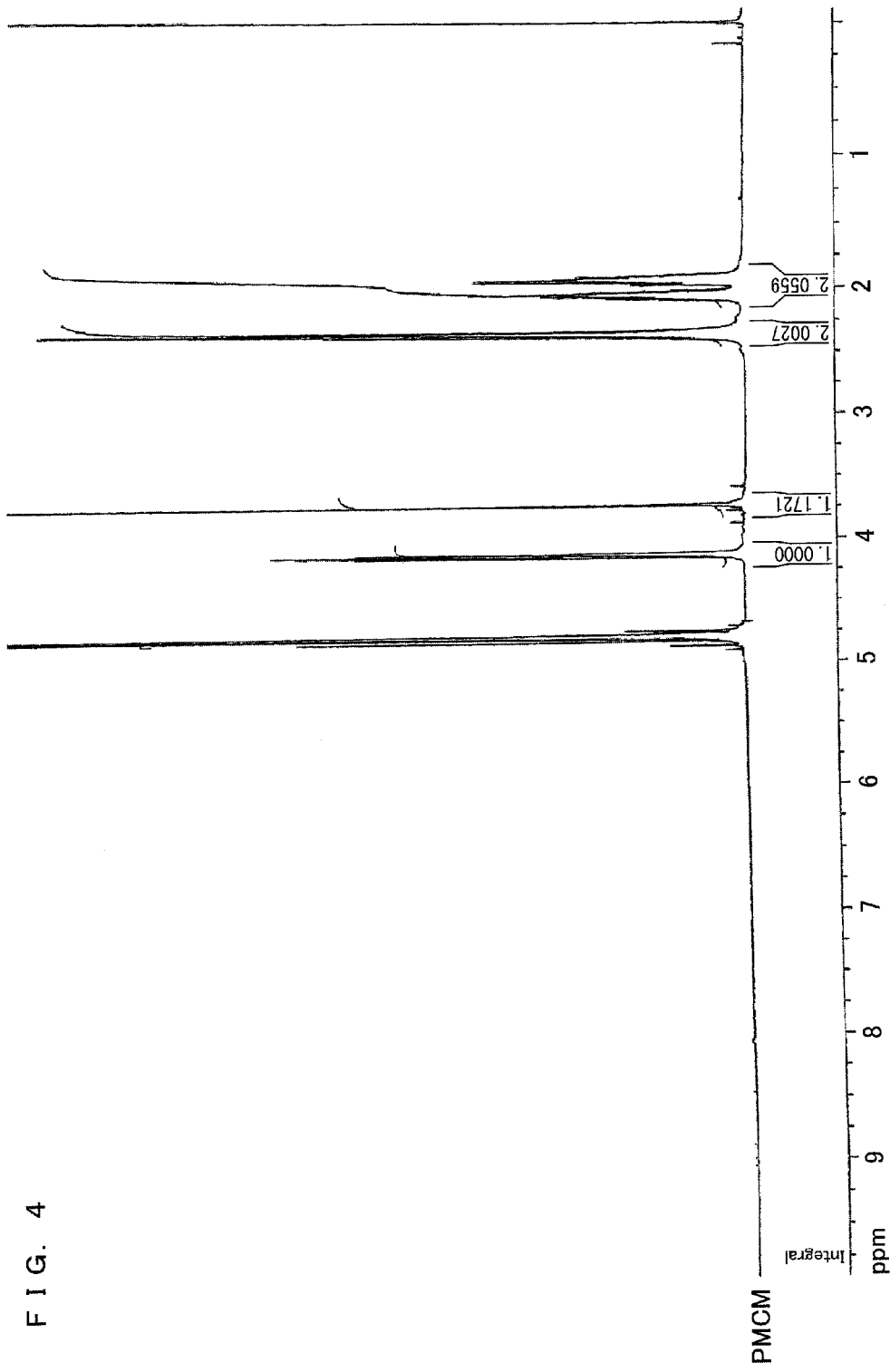
[FIG. 4] A drawing showing a H-NMR spectrum (500 MHz) for poly-γ-L-glutamate.

FIG. 4 is a H-NMR spectrum (500 MHz) for the poly-γ-L-glutamate obtained in example 4. The measurement was carried out using heavy water.

Example 8; Production of Poly-γ-L-Glutamate 0.4 mL of a PGA-producing liquid culture medium (22.5% NaCl, 2% $MgSO_4.7H_2O$, 0.2% KCl, 3% Trisodium Citrate, 1% yeast extract, 0.75% casamino acid) was added to an L dry ample of *Natrialba aegyptiaca* (Accession No.: FERM BP-10749) to obtain a suspension. 0.2 mL of the suspension was inoculated on a PGA agar medium (10% NaCl, 2% $MgSO_4.7H_2O$, 0.2% KCl, 3% Trisodium Citrate, 1% yeast extract, 0.75% casamino acid, 2% agar) and cultured at 37° C. for 3 days to obtain a single colony.

Next, 3 mL of a PGA-producing liquid culture medium (22.5% NaCl, 2% $MgSO_4.7H_2O$, 0.2% KCl, 3% Trisodium Citrate, 1% yeast extract, 0.75% casamino acid, pH 7.2) was put in five 18-mL test tubes. Furthermore, samples were scraped off the single colony, using an inoculation loop once for each sample, for subsequent inoculation. After the inoculation, the samples in the test tubes were cultured at 37° C. and 300 rpm for 3 days. 0.5 mL of the obtained culture solution was inoculated in ten 500-mL Sakaguchi flasks containing 50 mL of a PGA-producing liquid culture medium and cultured at 37° C. for 5 days. Subsequent to the culturing, the obtained culture solution was centrifuged to remove bacteria cells to collect supernatant.

Next, the collected supernatant was diluted with 3 times the amount of water and adjusted in pH with 1-N sulfuric acid to 3.0. After the pH adjustment, the supernatant was stirred at room temperature for 5 hours. Thereafter, the supernatant was diluted with 3 times the amount of ethanol and subjected to centrifugation to collect precipitate. This precipitate is no other than L-PGA.

The collected L-PGA was dissolved in a 0.1-mM Tris-HCl buffer solution (pH 8.0). The mixture was dialyzed to remove low-molecular-weight substances and other impurities. Next, to remove nucleic acid contained in the dialyzed liquid, $MgCl_2$, DNaseI (available from TAKARA Co.), and RNaseI (available from NIPPON GENE Co. Ltd.) were added to the liquid up to 1 mM, 10 U/mL, and 20 μg/mL and incubated at 37° C. for 2 hours. Next, proteinase K (available from TAKARA Co.) was added to the nucleic acid-free liquid up to 3 U/mL, and the mixture was incubated at 37° C. for 5 hours to remove protein for treatment with proteinase K.

After the treatment with proteinase K, the mixture was dialyzed with ultrapure water to remove low-molecular-weight substances. Next, the L-PGA was adsorbed by an anion exchange resin (Q sepharose Fast Flow, available from GE Healthcare Biosciences). After the resin was washed in a 0.5-M aqueous solution of NaCl, the glutamate was eluted with a 1-M aqueous solution of NaCl. The obtained solution was dialyzed further with ultrapure water. The dialyzed solution was freeze dried to obtain a sodium salt of L-PGA ("L-PGA.Na salt"). The ultrapure water had been prepared from Milli Q (pure water producing device made by Millipore).

Example 9

Molecular Weight Analysis of poly-γ-L-glutamate . . . 1

The average molecular weight of the L-PGA.Na salt obtained in example 8 was measured by GPC analysis. The analysis revealed that Mw was 7,522,000, Mn was 3,704,000, and Mw/Mn was 2.031 (in terms of pullulan).

The GPC analysis was carried out under the following conditions.
Device: HLC-8220 GPC (available from Tosoh Corporation)
Column: TSKgel α-M (available from Tosoh Corporation)
Flow rate: 0.6 mL/min,
Eluent: 0.15-M aqueous solution of NaCl
Column temperature: 40° C.
Amount supplied: 10 μL
Detector: differential thermal analyzer Example 10

Molecular Weight Analysis of poly-γ-L-glutamate . . . 2

L-PGA.Na salt was obtained by the same procedure as in example 8, except that the L-PGA adsorbed by an anion exchange resin was eluted in stages with a 0.7-M, a 0.8-M, and a 1.0-M aqueous solution of NaCl. The average molecular weight of the L-PGA.Na salt was measured by GPC analysis. The analysis revealed that Mw was 2,135,000, Mn was 1,021,000, and Mw/Mn was 2.091 for the L-PGA.Na salt obtained by the elution with the 0.7-M aqueous solution of NaCl and also that Mw was 7,522,000, Mn was 3,704,000, and Mw/Mn was 2.031 for the L-PGA.Na salt obtained by the elution with the 1.0-M aqueous solution of NaCl (in terms of pullulan). The GPC analysis in the present example was conducted by the same procedure as in example 9.

Example 11

Verification of poly-V-L-glutamate Structure

Figure 5:
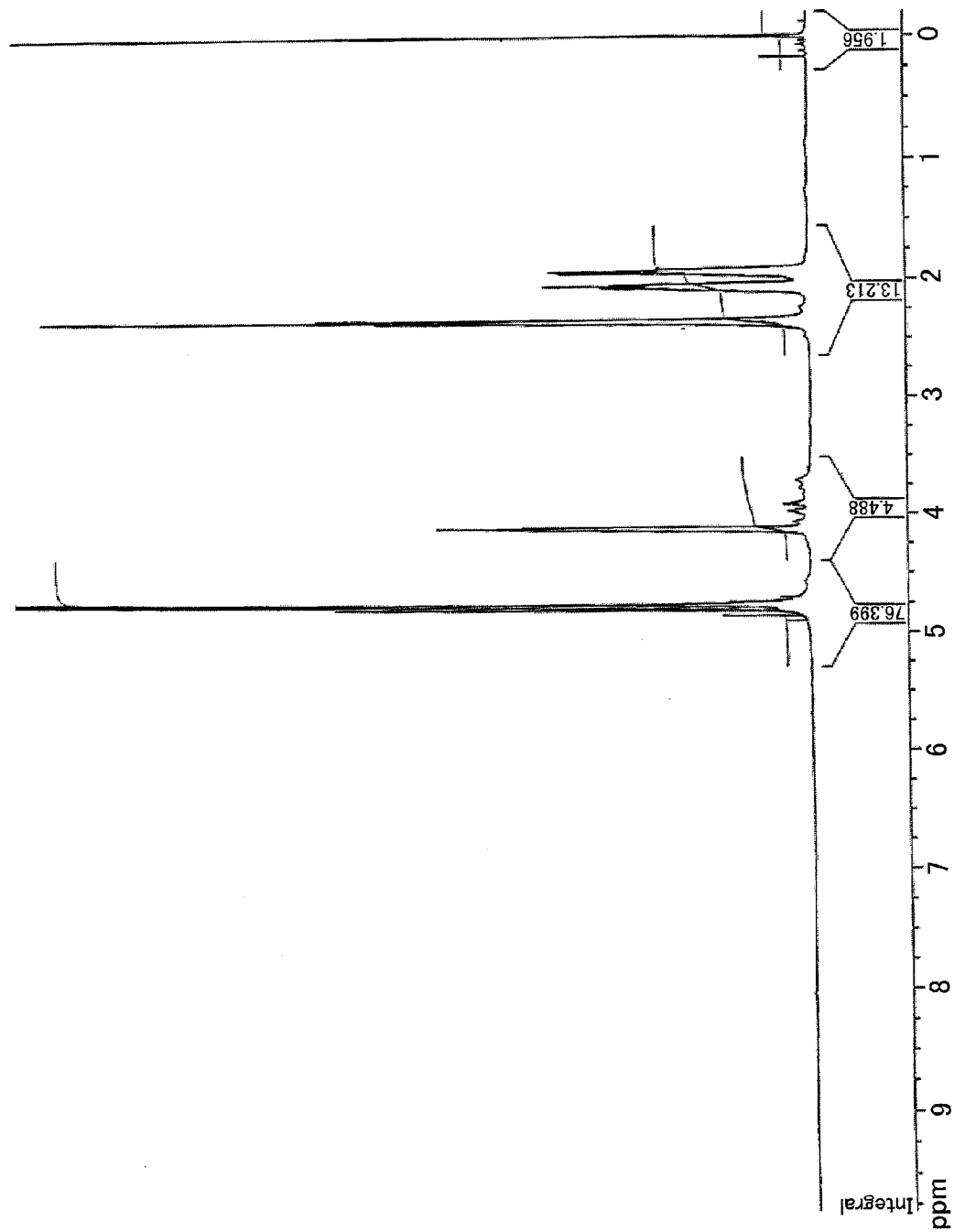
[FIG. 5] A drawing showing a H-NMR spectrum for the L-PGA obtained in an example of the present invention.

The L-PGA.Na salt obtained in example 8 was subjected to H-NMR to analyze the structure. Result is shown in FIG. 5. The H-NMR analysis was carried out under the following conditions.
Device: Fourier transform nuclear magnetic resonance apparatus (AVANCE 500 available from BRUKER)
Measurement solvent: Heavy water
Sample solution concentration: 0.5 to 1.0%,
$^1$H resonance frequency: 500 MHz,
Chemical shift reference: TSP (sodium trimethylsilylpropionate-2,2,3,3-d4)
δ=0.0 ppm Example 12

Evaluation of Hydrogel Production and Water Absorption Ratio

The present example investigated relationship between the dose of gamma radiation used to crosslink L-PGA, the concentration of the aqueous solution of L-PGA.Na salt irradiated with the irradiation with gamma rays, and the water absorption ratio of the obtained crosslinked L-PGA, by using two types of L-PGA-Na salt obtained in example 8 and example 10.

First, 2 wt % and 5 wt % aqueous solutions were made for the two types of L-PGA.Na salt, to obtain a total of four types of aqueous solutions of L-PGA.Na salt.

Next, the aqueous solutions of L-PGA.Na salt were bubbled with nitrogen for 3 minutes. A 2-mL sample was taken from each of the solutions and placed in a 10-mL lidded sample vial, and the lid was closed. As will be detailed later, six doses of gamma radiation would be investigated in the present example. For that purpose, six sample vials were prepared for each of the four types of aqueous solutions of L-PGA.Na salt. That is, a total of 24 vials.

Next, each sample vial was irradiated with gamma rays by using a gamma ray irradiator containing cobalt 60 as a radiation source. The six sample vials were irradiated up to respective doses of 1 kGy, 3 kGy, 5 kGy, 7 kGy, 10 kGy, and 20 kGy. The product obtained after the irradiation with gamma rays was taken out of the sample vials, passed through an 80-mesh metal net to remove excess water, and freeze dried to obtain crosslinked L-PGA powder. The excess water had contained uncrosslinked L-PGA and been removed primarily for the purpose of removing the uncrosslinked L-PGA.

Next, the obtained crosslinked L-PGA powder was put in an enough amount of water for the crosslinked L-PGA powder to swell. After being left to sit in the water for 1 week, the product was filtered with an 80-mesh metal net to remove uncrosslinked L-PGA. Hydrogel was hence obtained.

The water absorption ratio of the crosslinked L-PGA obtained in the present example was calculated by subtracting the dry weight of the crosslinked L-PGA powder used in the production of the hydrogel from the wet weight of the hydrogel obtained in the present example and dividing the difference by the dry weight of the crosslinked L-PGA powder.

Figure 6:
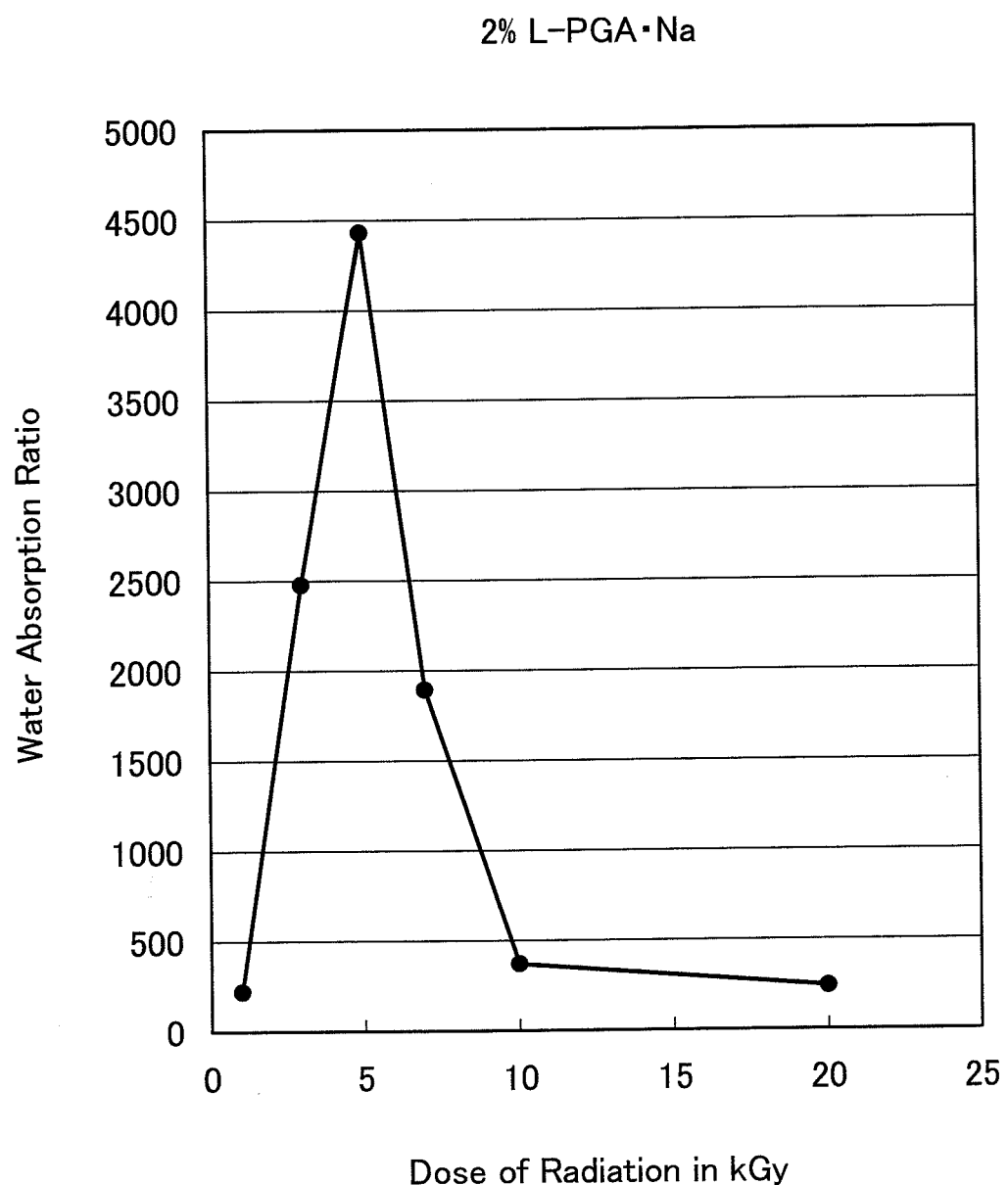
[FIG. 6] A drawing showing results of examination of relationship between the water absorption ratio of a crosslinked L-PGA obtained using a 2 wt % aqueous solution of a Na salt of L-PGA and the dose of gamma radiation emitted in the production of crosslinked L-PGA in an example of the present invention.
Figure 7:
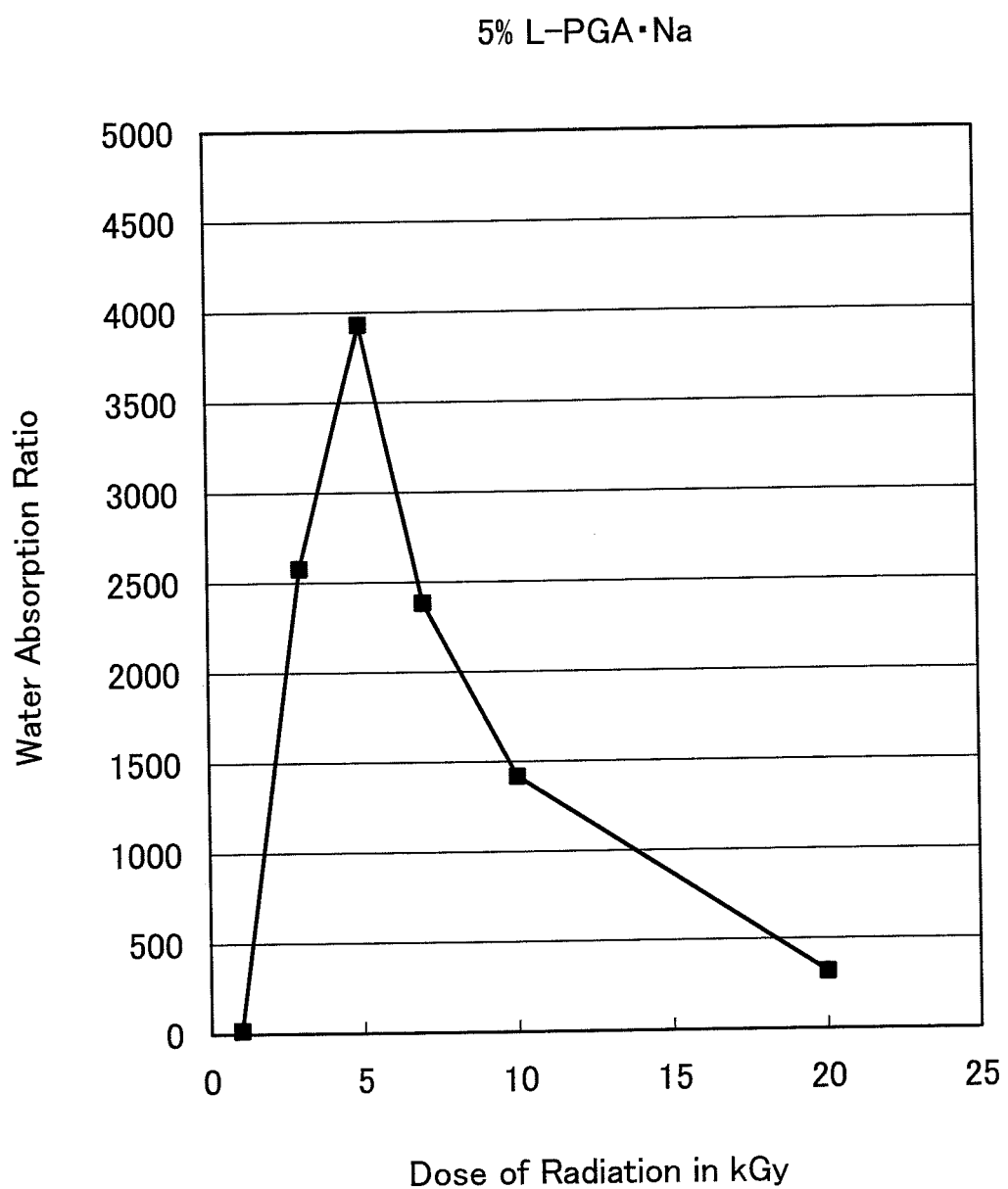
[FIG. 7] A drawing showing results of examination of relationship between the water absorption ratio of a crosslinked L-PGA obtained using a 5 wt % aqueous solution of a Na salt of L-PGA and the dose of gamma radiation emitted in the production of crosslinked L-PGA in an example of the present invention.

Table 1, Table 2, FIG. 6, and FIG. 7 show results comparison of relationships between calculated water absorption ratios of the L-PGA and the doses of γ exposure in the production of the crosslinked L-PGA. For Table 1 and FIG. 6, a 2 wt % aqueous solution of Na salt of L-PGA was used in the production of crosslinked L-PGA. FIG. 6 is a graphical representation of the numeric values in Table 1. For Table 2 and FIG. 7, a 5 wt % aqueous solution of Na salt of L-PGA was used in the production of crosslinked L-PGA. FIG. 7 is a graphical representation of the numeric values in Table 2. The numeric values in Tables 1 and 2 are average values of the water absorption ratios of the crosslinked L-PGA obtained from the aforementioned two types of L-PGA.Na salt. In FIGS. 6 and 7, the vertical axes indicate the water absorption ratio, whereas the horizontal axes indicate the dose of gamma radiation.

TABLE 1

| | Dose of Radiation | | | | | |
|---|---|---|---|---|---|---|
| | 1 kGy | 3 kGy | 5 kGy | 7 kGy | 10 kGy | 20 kGy |
| Water Absorption Ratio | 220 | 2,480 | 4,400 | 1,900 | 370 | 240 |

TABLE 2

| | Dose of Radiation | | | | | |
|---|---|---|---|---|---|---|
| | 1 kGy | 3 kGy | 5 kGy | 7 kGy | 10 kGy | 20 kGy |
| Water Absorption Ratio | 10 | 2,560 | 3,900 | 2,400 | 1,400 | 300 |

Table 1, Table 2, FIG. 6, and FIG. 7 show that the crosslinked L-PGA obtained in the present example had a water absorption ratio from 10 to 4,400, inclusive.

Example 13

Evaluation of Gelation Ratio

The present example investigated relationship between the dose of gamma radiation used to crosslink L-PGA and the gelation ratio in producing hydrogel from L-PGA.

First, the dry weight of the unirradiated L-PGA.Na salt used in example 12 was measured (the dry weight was designated "original L-PGA weight"). Next, the dry weight of the crosslinked L-PGA powder obtained in example 12 was measured (the weight was designated "crosslinked L-PGA weight"). The ratio (%) of the crosslinked L-PGA weight to the original L-PGA weight was calculated as the gelation ratio. The values in Table 3 are average values of the gelation ratios of the hydrogels produced using the four types of aqueous solutions of L-PGA.Na salt with respect to each dose of γ exposure for the aqueous solution of L-PGA.Na salt.

TABLE 3

| | Dose of Radiation | | | | | |
|---|---|---|---|---|---|---|
| | 1 kGy | 3 kGy | 5 kGy | 7 kGy | 10 kGy | 20 kGy |
| Gelation Ratio | 35 | 90 | 98 | 94 | 90 | 86 |

Example 14

Water Absorption Ratio of Different Lots of poly-γ-L-glutamate hydrogel

L-PGA was produced three times by the same method as in example 8 (the obtained L-PGA lots were designated lot A, lot B, and lot C respectively). Hydrogel was produced from lots A to C of L-PGA by the same method as in example 12. The dose of gamma radiation was 5 kGy. Furthermore, the water absorption ratios of the hydrogels obtained from lots A to C of L-PGA were calculated by the same method as in example 12. Results are shown in Table 4.

TABLE 4

| Lot | A | B | C |
|---|---|---|---|
| Water Absorption Ratio | 4,400 | 4,160 | 3,900 |

Table 4 demonstrates high reproducibility. Hydrogel of consistent property could be stably produced from different lots of L-PGA.

Comparative Example 1

Production of Hydrogel from poly-γ-DL-glutamate

Production of hydrogel of DL-PGA was attempted by the same procedure as in example 12, except that two types of sodium salt of DL-PGA (available from Wako Pure Chemical Ind.) were used. One of them had an average molecular weight of 1,500,000 to 2,500,000, and the other of 4,000,000 to 6,000,000. No hydrogel of DL-PGA could be obtained from the two types of sodium salt of DL-PGA. Therefore, the gelation ratios in producing DL-PGA hydrogel from DL-PGA are all zero shown in Table 5. Since no crosslinked DL-PGA could be obtained, the water absorption ratio could not be calculated.

TABLE 5

| | Dose of Radiation | | | | | |
|---|---|---|---|---|---|---|
| | 1 kGy | 3 kGy | 5 kGy | 7 kGy | 10 kGy | 20 kGy |
| L-PGA | 35 | 90 | 98 | 94 | 90 | 86 |
| DL-PGA | 0 | 0 | 0 | 0 | 0 | 0 |

Example 15

Production of Crosslinked poly-γ-L-glutamate

A 5% aqueous solution of L-PGA.Na salt obtained in example 8 was prepared.

Next, the aqueous solution of L-PGA.Na salt was bubbled with nitrogen for 3 minutes. A 2-mL sample was taken and placed in a 10-mL lidded sample vial, and the lid was closed.

Next, the sample vial was irradiated with gamma rays by using a gamma ray irradiator containing cobalt 60 as a radiation source. The sample vial was irradiated up to a dose of 5 kGy. The product obtained after the irradiation with gamma rays was taken out of the sample vial, passed through an 80-mesh metal net to remove excess water, and freeze dried to obtain crosslinked L-PGA powder. The excess water had contained uncrosslinked L-PGA and been removed primarily for the purpose of removing the uncrosslinked L-PGA.

Example 16

Evaluation of Moisture Retention Capability of poly-γ-L-glutamate Based on Dry Rough Skin Model LSE (Living Skin Equivalent) tissues were taken out according to the manual of a test skin kit (Code No. LSE-002, available from Toyobo Co., Ltd.). Next, the LSE tissues were set in an assay plate (part of the test skin kit) and left to sit in a dry state for 7 hours (in a $CO_2$ incubator set up to maintain temperature and relative humidity at 37° C. and 15% RH). Hence, dry rough skin models ("dry LSE tissues") were obtained. The model imitated keratin from which water evaporated.

Next, pure water, a 0.5% DL-PGA aqueous solution, a 2.5% DL-PGA aqueous solution, a 0.5% L-PGA aqueous solution, and a 2.5% L-PGA aqueous solution, each in the amount of 70 μL, were applied dropwise to the surface of the dry LSE tissues with a micro pipette. The Na salt of L-PGA obtained in example 8 was used as L-PGA, Na salt of DL-PGA from Wako Pure Chemical Ind. was used as DL-PGA.

Next, 600 μL of an assay culture medium (part of the test skin kit) was added to the bottom of the assay plate in which the dry LSE tissues were placed. After that, the assay was put to sit in a $CO_2$ incubator set up to maintain temperature and relative humidity at 37° C. and 15% RH for 24-hour incubation. Then, the dry LSE tissues were removed from the $CO_2$ incubator, and 600 μL of a liquid mixture of an assay culture medium (part of the test skin kit) containing 0.333 g/mL of a tetrazolium salt (MTT) reagent was put in an assay tray according to the manual of the test skin kit. The assay tray was incubated for 3 hours in a $CO_2$ incubator set up to maintain temperature and relative humidity at 37° C. and 15% RH to subject the dry LSE tissues to a treatment with MTT.

After the treatment, the center of the dry LSE tissues, along with the polycarbonate membrane below the dry LSE tissues, was hollowed with a biopsy punch (diameter 8 mm, available from Toyobo Co., Ltd.). Next, the removed piece was placed in a test tube. 300 μL of a 0.04-N hydrochloric acid-isopropanol was added. The mixture was left to sit in a dark place for 2 hours. Next, the solution in the test tube was stirred for sufficient blending. After that, the solution was subjected to centrifuged at 3,000 rpm for 5 minutes to obtain supernatant. Next, the amount of blue-violet formazan contained in 200 μL of the supernatant was calculated by measuring absorption of 572-nm light.

Figure 8:
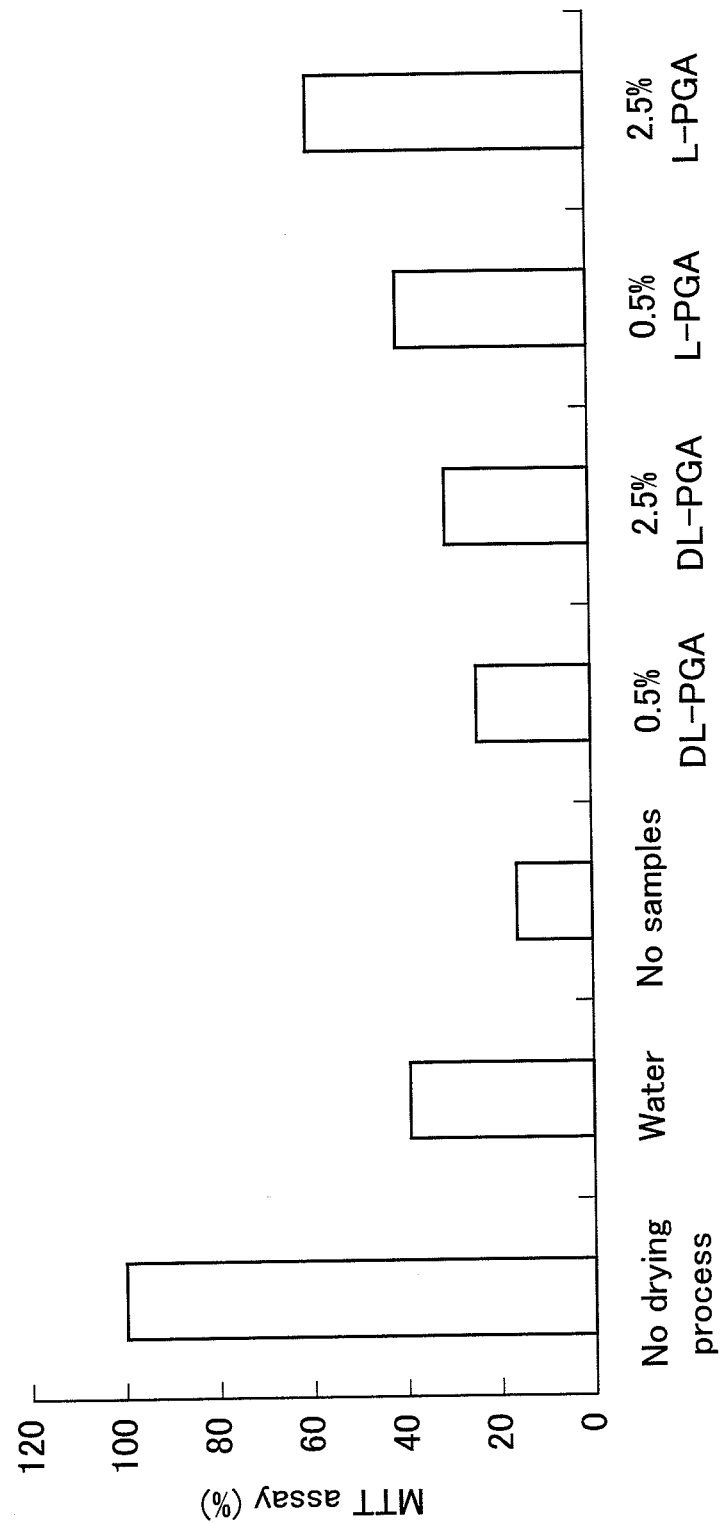
[FIG. 8] A drawing showing results of evaluation of moisture retention capability in an example of the present invention.

Results are shown in FIG. 8. FIG. 8 is a drawing showing results of evaluation of moisture retention capability. The vertical axis indicates the amount of formazan (light absorption) in percentage to the amount of formazan extracted from the LSE tissues to which no drying process was done. The horizontal axis shows sample types. In FIG. 8, "No drying process" indicates that no drying process was carried out on the LSE tissues. "No samples" indicates that none of pure water, a DL-PGA aqueous solution, and an L-PGA aqueous solution was applied to the LSE tissues which had been subjected to a drying process. In other words, FIG. 8 shows results of measurement of the amount of formazan for samples which were not subjected to a drying process and which was treated directly with MTT and also shows results of measurement of the amount of formazan for the aforementioned dry LSE tissues which were treated directly with MTT.

There is close relationship between the light absorption (amount of formazan) obtained by the method described in the present example and rough skin healing effect. The evaluation method above is a quantitative, simple, economical, and effective method of evaluating healing of dry rough human skin.

As appreciated from FIG. 8, the amount of formazan, that is, the rough skin recovery rate, was 30% after dropwise application of a 2.5% aqueous solution of a commercial DL-PGA used conventionally as a moisture retention agent. Meanwhile, the rough skin recovery rate was 60% after dropwise application of a 2.5% aqueous solution of L-PGA. These facts demonstrate that L-PGA exhibited about twice the rough skin recovery rate of the conventional commercial product and had higher moisture retention capability than that product.

Example 17

Moisture Retention Effect of Crosslinked poly-γ-L-glutamate Hydrogel in Human Skin Roughness Test A 0.5% solution of SDS was contacted to the inner side of a human upper arm for 10 minutes for treatment with SDS to make rough skin. Meanwhile, a hydrogel was prepared by mixing the crosslinked L-PGA powder obtained in example 16 with water to a concentration of 0.15%.

Next, the hydrogel was applied to the rough skin on the inner side of a human upper arm. The trial subject stayed in a room maintained at constant temperature (=23° C.) and constant humidity (=45%) for 1 hour. After that, the skin keratin water content of the skin of the subject (sample D) was measured with a keratin water content meter (product name: Skicon, available from I.B.S. Co., Ltd.).

Similar measurement of keratin water content was carried out on more skin samples of the inner side of a human upper arm. Sample A was the skin before being treated with SDS. Sample B was taken after the treatment with SDS, but before the application of the hydrogel. Sample C was taken after treating the skin with SDS, applying water, instead of the hydrogel, to the skin, and having the trial subject stay in the room under the same conditions as in sample D.

Results are shown in FIG. 9. FIG. 9 is a drawing showing results of a human skin roughness test. The vertical axis indicates skin keratin water content. The horizontal axis indicates the sample types. In FIG. 9, A to D refer to samples A to D respectively.

As shown in FIG. 9, sample D had a high skin keratin water content, which demonstrated that keratin water content had recovered.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

Industrial Applicability

The present invention enables mass production of uniform optical purity, large molecular weight poly-γ-L-glutamate by liquid culture or a like method. More specifically, the present invention enables high productivity preparation of poly-γ-L-glutamate with uniform optical purity and having a number average molecular weight of 1,300,000 or greater in an amount of 4.99 g or more per liter of culture solution.

As described in the foregoing, the crosslinked L-PGA in accordance with the present invention has a crosslinked structure between L-PGA molecules. The feature results in the advantage of being able to stably provide biodegradable, highly water absorbent crosslinked L-PGA with desired quality.

The method of producing the crosslinked L-PGA in accordance with the present invention involves the crosslinking step of crosslinking L-PGA molecules with each other. The feature results in the advantage of being able to stably provide biodegradable, highly water absorbent crosslinked L-PGA with desired quality. Furthermore, a high gelation ratio in producing the crosslinked L-PGA from L-PGA results in the advantage of being able to produce crosslinked L-PGA with high producing efficiency.

The hydrogel in accordance with the present invention contains the L-PGA in accordance with the present invention. The feature results in the advantage of being able to stably produce hydrogel with desired quality.

The external dermal agent in accordance with the present invention, as described in the foregoing, contains at least either the L-PGA or crosslinked the L-PGA. The feature results in the advantage of being able to stably provide an external dermal agent with desired quality. In other words, the L-PGA has only L-glutamate being linked; therefore its optical activity is uniform, and molecular weight is large, providing excellent moisture retention capability. By including L-PGA and/or crosslinked L-PGA into an external dermal agent, the external dermal agent with desired quality can be stably produced.

The L-PGA and crosslinked L-PGA have excellent moisture retention capability. The feature results in the advantage of being able to provide an external dermal agent that is especially useful as a cosmetics material and a moisture retention agent.

The present invention enables mass production of uniform optical purity, large molecular weight poly-γ-L-glutamate by liquid culture or a like method. Culturing is made very easy. The invention is expected to make large contributions to industry.

The crosslinked L-PGA in accordance with the present invention and the hydrogel in accordance with the present invention are applicable in various fields like health care (e.g., disposable diapers), medical products, architecture, foods, agriculture, and gardening.

Furthermore, the present invention is expected to make especially large contributions to the cosmetics industry by providing poly-γ-L-glutamate with uniform optical purity and large molecular weight and crosslinked poly-γ-L-glutamate, as well as resultant external dermal agents with greater moisture retention capability than conventional products.

Name of Depository: International Patent Organism Depository (IPOD), National Institute of Advanced Industrial Science and Technology Address of Depository: AIST Tsukuba Central 6, 1-1, Higashi 1-chome Tsukuba-shi, Ibaraki 305-8566 Japan Date of Depository: Apr. 4, 2006

Accession No.: IPOD FERM BP-10747

Name of Depository: International Patent Organism Depository (IPOD), National Institute of Advanced Industrial Science and Technology Address of Depository: AIST Tsukuba Central 6, 1-1, Higashi 1-chome Tsukuba-shi, Ibaraki 305-8566 Japan Date of Accession: Apr. 4, 2006

Accession No.: IPOD FERM BP-10748

Name of Depository: International Patent Organism Depository (IPOD), National Institute of Advanced Industrial Science and Technology Address of Depository: AIST Tsukuba Central 6, 1-1, Higashi 1-chome Tsukuba-shi, Ibaraki 305-8566 Japan Date of Accession: Apr. 4, 2006

Accession No.: IPOD FERM BP-10749

The invention claimed is:

1. An isolated microorganism of *Natrialba aegyptiaca* strain 0830-82 (Accession No.: FERM BP-10747).

2. A method of producing poly-γ-L-glutamate comprising the steps of:
   (a) culturing the microorganism of claim 1 so as to produce a culture solution containing poly-γ-L-glutamate having large molecular weight, and
   (b) collecting the poly-γ-L-glutamate from the culture solution obtained by the culturing of step (a).

3. The method of claim 2, wherein the culture solution contains 5 to 30 W/V % salt.

4. An isolated microorganism of *Natrialba aegyptiaca* strain 0830-243 (Accession No.: FERM BP-10748).

5. A method of producing poly-γ-L-glutamate comprising the steps of:
   (a) culturing the microorganism of claim 4 so as to produce a culture solution containing poly-γ-L-glutamate having large molecular weight, and
   (b) collecting the poly-γ-L-glutamate from the culture solution obtained by the culturing of step (a).

6. The method of claim 5, wherein the culture solution contains 5 to 30 W/V % salt.

7. An isolated microorganism of *Natrialba aegyptiaca* strain 0831-264 (Accession No.: FERM BP-10749).

8. A method of producing poly-γ-L-glutamate comprising the steps of:
 (a) culturing the microorganism of claim 7 so as to produce a culture solution containing poly-γ-L-glutamate having large molecular weight, and (b) collecting the poly-γ-L-glutamate from the culture solution obtained by the culturing of step (a).

9. The method of claim 8, wherein the culture solution contains 5 to 30 W/V % salt.

* * * * *